US008871906B2

(12) United States Patent
Pastan et al.

(10) Patent No.: US 8,871,906 B2
(45) Date of Patent: Oct. 28, 2014

(54) DELETIONS IN DOMAIN II OF PSEUDOMONAS EXOTOXIN A THAT REMOVE IMMUNOGENIC EPITOPES

(75) Inventors: Ira H. Pastan, Bethesda, MD (US); John Weldon, Bethesda, MD (US); David FitzGerald, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 681 days.

(21) Appl. No.: 12/676,203

(22) PCT Filed: Sep. 4, 2008

(86) PCT No.: PCT/US2008/075296
§ 371 (c)(1),
(2), (4) Date: May 11, 2010

(87) PCT Pub. No.: WO2009/032954
PCT Pub. Date: Mar. 12, 2009

(65) Prior Publication Data
US 2010/0215656 A1    Aug. 26, 2010

Related U.S. Application Data

(60) Provisional application No. 60/969,929, filed on Sep. 4, 2007, provisional application No. 61/018,853, filed on Jan. 3, 2008.

(51) Int. Cl.
*C07K 14/21* (2006.01)
*A61K 38/00* (2006.01)

(52) U.S. Cl.
CPC ............. *C07K 14/21* (2013.01); *A61K 38/00* (2013.01); *C07K 2319/30* (2013.01)
USPC .......................... 530/351; 424/260.1

(58) Field of Classification Search
CPC ........................................ C07K 14/21
USPC .................. 424/236.1, 260.1; 530/350, 351
See application file for complete search history.

(56) References Cited

U.S. PATENT DOCUMENTS 4,235,871 A    11/1980   Papahadjopoulos et al.
4,458,066 A     7/1984   Caruthers et al.
(Continued)

FOREIGN PATENT DOCUMENTS

EP    0 404 097 A2    12/1990
EP    0583794    *    2/1994    ............. C12N 15/00
(Continued)

OTHER PUBLICATIONS

Rutault, K et al, Infection and Immunity, Dec. 1993, vol. 61(12), pp. 5417-5420, Comparative immunochemistry of two fragments from Domain Ib and III of *Pseudomonas aeruginosa* Exotoxin A.*

(Continued)

*Primary Examiner* — Albert Navarro
*Assistant Examiner* — Ginny Portner
(74) *Attorney, Agent, or Firm* — Leydig, Voit & Mayer

(57) ABSTRACT

The invention provides mutated, cytotoxic forms of *Pseudomonas* exotoxin A (PE) comprising a furin cleavage sequence conjugated or fused directly to residues 395-613 of PE or variants of that sequence. These minimal forms of PE are smaller than previous cytotoxic forms of PE, reduce non-specific toxicity, and reduce immunogenicity due to domain II or domain Ib of PE. The invention further provides nucleic acids encoding said PEs, chimeric molecules containing them, and methods of use thereof.

41 Claims, 6 Drawing Sheets

(56) References Cited

U.S. PATENT DOCUMENTS

Figure 1:
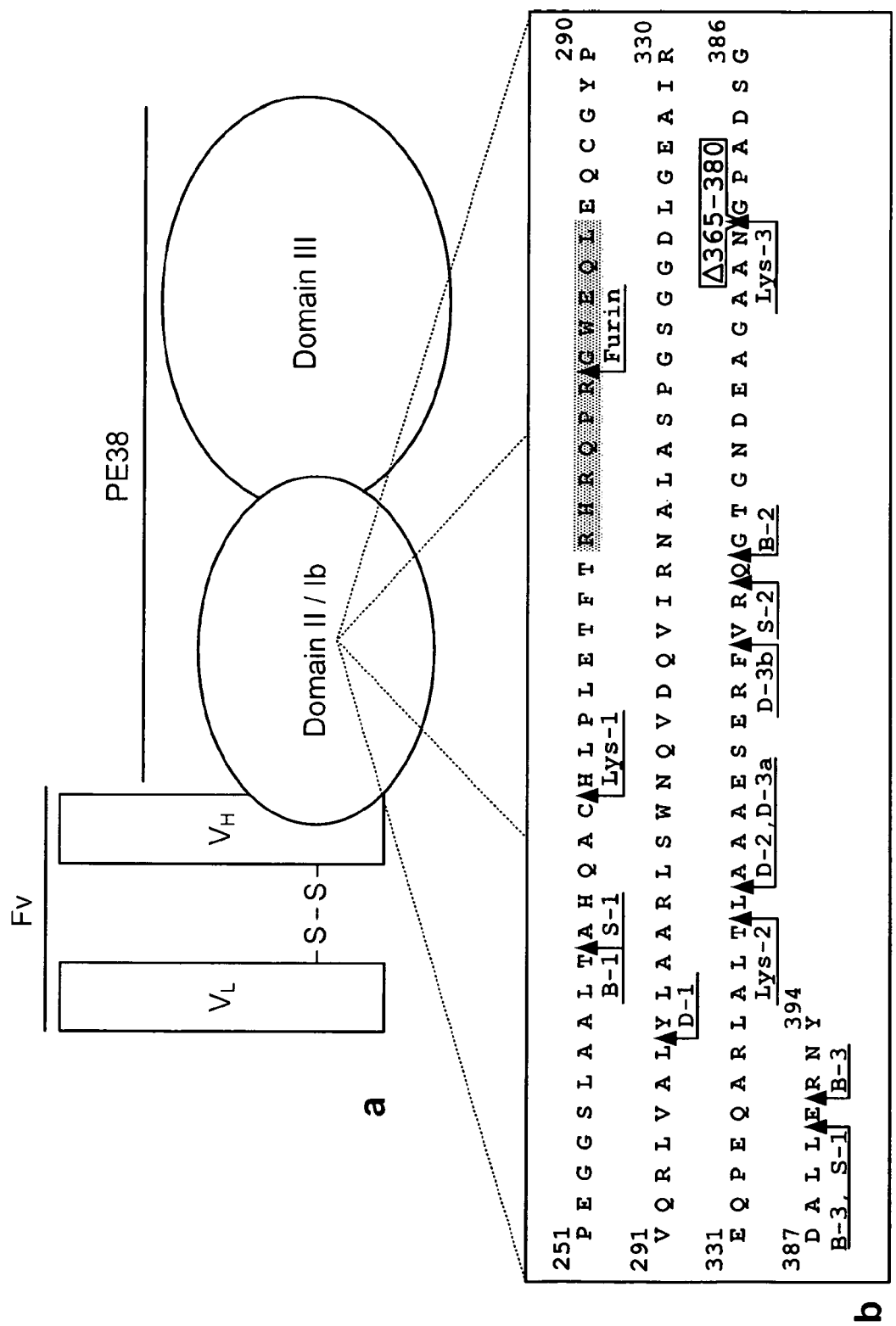
Figure 2:
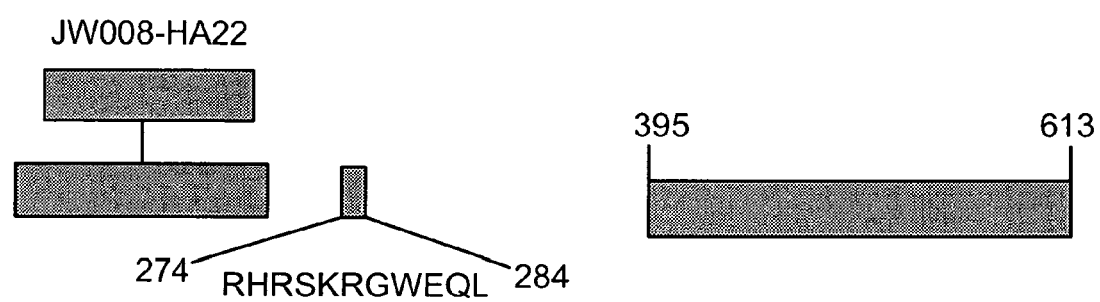
Figure 4:
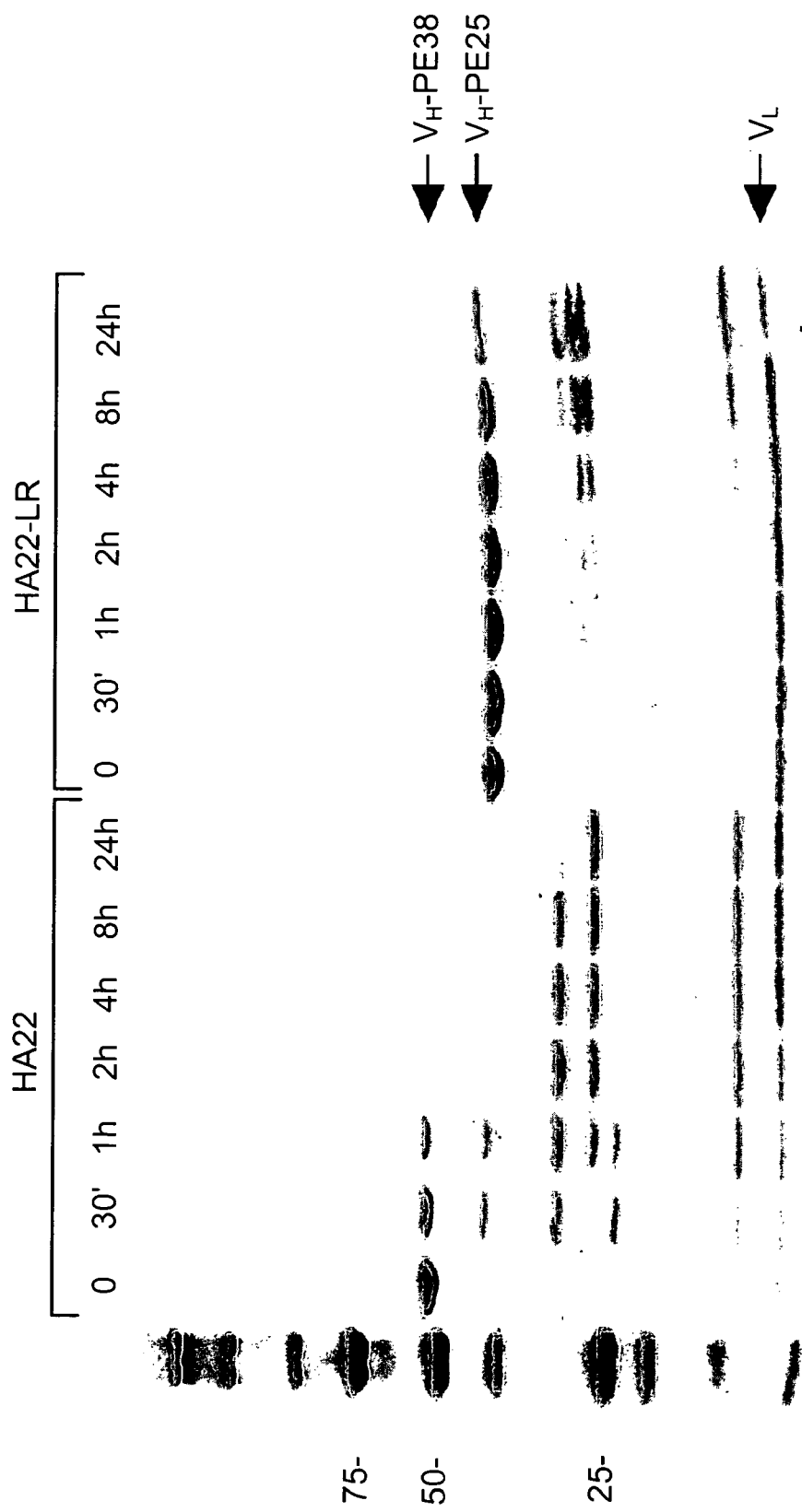

| | | | |
|---|---|---|---|
| 4,501,728 A | | 2/1985 | Geho et al. |
| 4,545,985 A * | | 10/1985 | Pastan et al. ............. 424/180.1 |
| 4,837,028 A | | 6/1989 | Allen |
| 4,892,827 A * | | 1/1990 | Pastan et al. ................. 435/193 |
| 4,902,505 A | | 2/1990 | Pardridge et al. |
| 4,957,735 A | | 9/1990 | Huang |
| 5,004,697 A | | 4/1991 | Pardridge |
| 5,019,369 A | | 5/1991 | Presant et al. |
| 5,055,303 A | | 10/1991 | Riley, Jr. |
| 5,188,837 A | | 2/1993 | Domb |
| 5,254,342 A | | 10/1993 | Shen et al. |
| 5,268,164 A | | 12/1993 | Kozarich et al. |
| 5,271,961 A | | 12/1993 | Mathiowitz et al. |
| 5,413,797 A | | 5/1995 | Khan et al. |
| 5,492,893 A * | | 2/1996 | Nett et al. ....................... 514/9.9 |
| 5,506,206 A | | 4/1996 | Kozarich et al. |
| 5,512,658 A * | | 4/1996 | Pastan et al. ................. 530/350 |
| 5,514,670 A | | 5/1996 | Friedman et al. |
| 5,534,496 A | | 7/1996 | Lee et al. |
| 5,587,455 A * | | 12/1996 | Berger et al. ................. 530/324 |
| 5,591,631 A * | | 1/1997 | Leppla et al. ............. 435/252.3 |
| 5,591,828 A | | 1/1997 | Bosslet et al. |
| 5,602,095 A | | 2/1997 | Pastan et al. |
| 5,608,039 A | | 3/1997 | Pastan et al. |
| 5,635,599 A * | | 6/1997 | Pastan et al. ................. 530/351 |
| 5,696,237 A * | | 12/1997 | FitzGerald et al. ........ 530/387.3 |
| 5,705,156 A * | | 1/1998 | Pastan et al. ............. 424/183.1 |
| 5,747,654 A | | 5/1998 | Pastan et al. |
| 5,821,238 A | | 10/1998 | Pastan et al. |
| 5,854,044 A | | 12/1998 | Pastan et al. |
| 5,888,773 A | | 3/1999 | Jost et al. |
| 6,086,900 A * | | 7/2000 | Draper ...................... 424/282.1 |
| 6,426,075 B1 * | | 7/2002 | Fitzgerald et al. ......... 424/260.1 |
| 6,558,672 B1 | | 5/2003 | Pastan et al. |
| 6,566,073 B1 * | | 5/2003 | Rivera et al. .................... 435/7.1 |
| 6,653,088 B1 * | | 11/2003 | Czech et al. .................... 435/7.1 |
| 6,825,325 B1 * | | 11/2004 | Fischer et al. ............. 530/388.2 |
| 7,081,518 B1 | | 7/2006 | Pastan et al. |
| 7,355,012 B2 * | | 4/2008 | Pastan et al. ............. 530/387.3 |
| 7,521,054 B2 * | | 4/2009 | Pastan et al. ............. 424/178.1 |
| 7,579,010 B2 * | | 8/2009 | Hunt .......................... 424/236.1 |
| 7,964,200 B2 * | | 6/2011 | Mrsny et al. .............. 424/263.1 |
| 7,999,077 B2 * | | 8/2011 | Pastan et al. ............. 530/387.1 |
| 8,092,806 B2 * | | 1/2012 | Wallach et al. ............ 424/185.1 |
| 8,598,318 B2 * | | 12/2013 | Lyman et al. ................. 530/351 |
| 2003/0185825 A1 * | | 10/2003 | Neville et al. ............. 424/144.1 |
| 2003/0211112 A1 * | | 11/2003 | Debinski ................... 424/178.1 |
| 2004/0136959 A1 * | | 7/2004 | Puri ............................ 424/93.2 |
| 2004/0146516 A1 | | 7/2004 | Roben et al. |
| 2006/0030007 A1 * | | 2/2006 | Byrd et al. ................... 435/69.7 |
| 2006/0104993 A1 * | | 5/2006 | Mrsny ........................ 424/235.1 |
| 2006/0149037 A1 * | | 7/2006 | Chakrabarty et al. ........ 530/350 |
| 2006/0153798 A1 * | | 7/2006 | Mrsny ......................... 424/85.1 |
| 2006/0193771 A1 * | | 8/2006 | Pastan et al. ................ 424/1.49 |
| 2007/0189962 A1 | | 8/2007 | Pastan et al. |
| 2008/0287356 A1 * | | 11/2008 | Wallach et al. ................. 514/12 |
| 2009/0142341 A1 * | | 6/2009 | Pastan et al. ............. 424/133.1 |
| 2009/0214543 A1 * | | 8/2009 | Zangemeister-Wittke et al. ........................... 424/138.1 |
| 2010/0215670 A1 * | | 8/2010 | Cizeau et al. ............. 424/178.1 |
| 2011/0250199 A1 * | | 10/2011 | Fitzgerald et al. ......... 424/134.1 |
| 2012/0276190 A1 * | | 11/2012 | Fitzgerald ..................... 424/450 |
| 2014/0094417 A1 * | | 4/2014 | Pastan et al. ................. 514/19.3 |

FOREIGN PATENT DOCUMENTS

| | | | | |
|---|---|---|---|---|
| WO | WO 93/11161 A1 | | 6/1993 | |
| WO | 98/20135 | * | 5/1998 | ............ C12N 15/31 |
| WO | WO 98/20135 A2 | | 5/1998 | |
| WO | WO 99/51643 A1 | | 10/1999 | |
| WO | 99/60135 | * | 11/1999 | ............ C12N 15/62 |
| WO | WO 02/40545 A2 | | 5/2002 | |
| WO | WO 03/084469 A2 | | 10/2003 | |
| WO | WO 2007/016150 A2 | | 2/2007 | |
| WO | WO 2008/052322 A1 | | 5/2008 | |

OTHER PUBLICATIONS

Kihara, Ako e tal, Cancer Research, vol. 54, pp. 5154-5159, Small chimeric toxins containing only transfroming growth factor alpha and Domain III of pseudomonas exotoxin with Good antitumor Activity in mice.*

Gaken, J et al, Gene Therappy, 2000, vol. 7, pp. 1979-1985, Viral transfer technology, Fusagene vectos: a novel strategy for the expression of multiple genes from a single cistron.*

Wang, T et al, Cancer Research, 2007, vol. 67, pp. 11830-11839, Recombinant Immunoproapoptotic Proteins with Furin Site Can Translocate and Kill HER2-Positive Cancer Cells.*

Edwards, Gwynneth M et al, Molecular and Cellular Biology, Jul. 1989, pp. 2860-2867, Epidermal Growth Factor Receptor Binding is affected by Structural Determinants in the Toxin Domain of Transforming Growth Factor Alpha Pseudomonas Exotoxin Fusion Proteins.*

Siegall, Clay B et al, Functional Analysis of Domains II, Ib, and III of *Pseudomonas aeruginosa* Exotoxin, The Journal of Biological Chemistry, vol. 264(24), pp. 14256-14261, 1989.*

Weldon, John E et al, Blood, Apr. 16, 2009, vol. 113(16), pp. 3792-3800, A protease resistant immunotoxin against CD22 with greatly increase activity against CLL and diminished animal toxicity, pp. 1-24.*

Southwick, FS et al, Infection and Immunity, 1995, vol. 63(1), gages 82-87, Proteolytic Activation of Bacterial Toxins by Eukaryotidc Cells is performed by furin and by additional Cellular Proteases.*

Mansfield, E., et al., "Characterization of RFB4-*Pseudomonas* Exotoxin A Immunotoxins Targeted to CD22 on B-Cell Malignancies," *Bioconiugate Chem.*, vol. 5, No. 7, pp. 557-563. (Sep. 1, 1996).

Onda, M., et al., "Characterization of the B Cell Epitopes Associates with a Truncated Form of *Pseudomonas* Exotoxin (PE38) Used to Make Immunotoxins for the Treatment of Cancer Patients," *The Journal of Immunology*, vol. 177, No. 12, pp. 8822-8834 (Dec. 1, 2006).

Schwemmlein, M., et al., "A CD19-specific single-chain immunotoxin mediates potent apoptosis of B-lineage leukemic cells," *Leukemia*, vol. 21, pp. 1405-1412 (May 10, 2007).

Altschul et al., "Basic local alignment search tool," *J. Mol. Biol.*, 215 (3), 403-410 (1990).

Altschul et al., "Gapped BLAST and PSI-BLAST: a new generation of protein database search programs," *Nucl. Acids Res.*, 25 (17), 3389-3402 (1977).

Arndt et al., "Helix-stabilized Fv (hsFv) antibody fragments: substituting the constant domains of a Fab fragment for a heterodimeric coiled-coil domain," *J. Mot. Biol.*, 312 (1), 221-228 (2001).

Bang et al., "HA22 (R490A) Is a Recombinant Immunotoxin with Increased Antitumor Activity Without an Increase in Animal Toxicity," *Clin. Can. Res.*, 11, 1545-1550 (2005).

Beaucage et al., "Deoxynucleoside phosphoramidites—A new class of key intermediates for deoxypolynucleotide synthesis," *Tetra. Lett.*, 22 (20), 1859-1862 (1981).

Bourdenet et al., "Biochemical and immunochemical studies of proteolytic fragments of exotoxin A from *Pseudomonas aeruginosa*," *Eur. J. Biochem.*, 192 (2), 379-385 (1990).

Bravo et al., "Accurate and efficient cleavage of the human insulin proreceptor by the human proprotein-processing protease furin. Characterization and kinetic parameters using the purified, secreted soluble protease expressed by a recombinant baculovirus," *J. Biol. Chem.*, 269 (41), 25830-25837 (1994).

Brenner et al., "Glomerular permselectivity: barrier function based on discrimination of molecular size and charge," *Am. J. Physiol.*, 234 (6), F455-F460 (1978).

Brinkmann, "Recombinant immunotoxins: protein engineering for cancer therapy," *Mol. Med. Today*, 2 (10), 439-446 (1996).

Brown "The epidermal growth factor/transforming growth factor-αfamily and their receptors," *Eur. J. Gastroenterol. Hepatol.*, 7, 914-922 (1995).

(56) References Cited

OTHER PUBLICATIONS

Brown et al., "Chemical synthesis and cloning of a tyrosine tRNA gene," *Methods Enzymol.*, 68, 109-151 (1979).

Buchner et al., "A method for increasing the yield of properly folded recombinant fusion proteins: single-chain immunotoxins from renaturation of bacterial inclusion bodies," *Anal. Biochem.*, 205 (2), 263-270 (1992).

Davies et al., "Antibody VH Domains as Small Recognition Units," *Biotechnology*, 13, 475-479 (1995).

Debinski et al., "Substitution of foreign protein sequences into a chimeric toxin composed of transforming growth factor alpha and *Pseudomonas* exotoxin," *Mol. Cell. Biol.*, 11 (3), 1751-1753 (1991).

Deussing et al., "Cathepsins B and D are dispensable for major histocompatibility complex class II-mediated antigen presentation," *Proc. Natl. Acad. Sci. USA*, 95 (8), 4516-4521 (1998).

Drexler et al., "DNA profiling and cytogenetic analysis of cell line WSU-CLL reveal cross-contamination with cell line REH (pre B-ALL)," *Leukemia*, 16 (9), 1868-1870 (2002).

Duckert et al., "Prediction of proprotein convertase cleavage sites," *Prot. Eng.*, 17 (1), 107-112 (2004).

Fitzgerald et al., "Why toxins!," *Semin. Cancer Biol.*, 7 (2), 87-95 (1996).

Fults et al., "Sustained-Release of Urease from a Poloxamer Gel Matrix," *J. Parent. Sci. Tech.*, 44 (2), 58-65 (1990).

Ghahroudi et al., "Selection and identification of single domain antibody fragments from camel heavy-chain antibodies," *FEBS Lett.*, 414, 521-526 (1997).

Hassan et al., "Phase I study of SS1P, a recombinant anti-mesothelin immunotoxin given as a bolus I.V. infusion to patients with mesothelin-expressing mesothelioma, ovarian, and pancreatic cancers," *Clin. Cancer Res.*, 13 (17), 5144-5149 (2007).

Hatsuzawa et al., "Purification and characterization of furin, a Kex2-like processing endoprotease, produced in Chinese hamster ovary cells," *J. Biol. Chem.*, 267 (23), 16094-16099 (1992).

Henikoff et al., "Amino acid substitution matrices from protein blocks," *Proc. Natl. Acad. Sci. USA*, 89 (22), 10915-10919 (1992).

Holliger et al., "Diabodies: small bivalent and bispecific antibody fragments," *Proc. Natl. Acad. Sci. USA*, 90, 6444-6448 (1993).

Holt et al., "Domain antibodies: proteins for therapy," *Trends Biotech.*, 21 (11), 484-490 (2003).

Huse et al., "Generation of a Large Combinatorial Library of the Immunoglobulin Repertoire in Phage Lambda," *Science*, 246, 1275-1281 (1989).

Hwang et al., "Functional domains of *Pseudomonas* exotoxin identified by deletion analysis of the gene expressed in *E. coli*," *Cell*, 48 (1), 129-136 (1987).

Ijntema et al., "Hydroxyapatite microcarriers for biocontrolled release of protein drugs," *Int. J. Pharm.*, 112 (3), 215-224 (1994).

Jinno et al., "Domain II mutants of *Pseudomonas* exotoxin deficient in translocation," *J. Biol. Chem.*, 264 (27), 15953-15959 (1989).

International Preliminary Report on Patentability, Application No. PCT/US2008/075296, dated Mar. 9, 2010.

International Search Report, Application No. PCT/US2008/075296, dated Dec. 8, 2008.

Johnston et al., "Sustained delivery of interleukin-2 from a poloxamer 407 gel matrix following intraperitoneal injection in mice," *Pharm. Res.*, 9 (3), 425-434 (1992).

Karlin et al., "Applications and statistics for multiple high-scoring segments in molecular sequences," *Proc. Natl. Acad. Sci. USA*, 90, 5873-5787 (1993).

Kasturi et al., "Alanine Scanning Mutagenesis Identifies Surface Amino Acids on Domain II of *Pseudomonas* Exotoxin Required for Cytotoxicity, Proper Folding, and Secretion into Periplasm," *J. Biol. Chem.*, 267 (32), 23427-23433 (1992).

Kihara et al., "Analysis of Sequences Required for the Cytotoxic Action of a Chimeric Toxin Composed of *Pseudomonas* Exotoxin and Transforming Growth Factor aα," *Bioconjugate Chem.*, 5 (6), 532-538 (1994).

Kondo et al., "Activity of immunotoxins constructed with modified *Pseudomonas* exotoxin A lacking the cell recognition domain," *J. Biol. Chem.*, 263 (19), 9470-9475 (1988).

Kreitman et al., "Cytotoxic activity of disulfide-stabilized recombinant immunotoxin RFB4(dsFv)-PE38 (BL22) toward fresh malignant cells from patients with B-cell leukemias," *Clin. Cancer Res.*, 6 (4), 1476-1487 (2000).

Kreitman et al., "Efficacy of the anti-CD22 recombinant immunotoxin BL22 in chemotherapy-resistant hairy-cell leukemia," *New Engl. J. Med.*, 345 (4), 241-247 (2001).

Kreitman et al., "Importance of the glutamate residue of KDEL in increasing the cytotoxicity of *Pseudomonas* exotoxin derivatives and for increased binding to the KDEL receptor," *Biochem. J.*, 307 (Pt. 1), 29-37 (1995).

Kreitman et al., "Phase I trial of recombinant immunotoxin anti-Tac(Fv)-PE38 (LMB-2) in patients with hematologic malignancies," *J. Clin. Oncol.*, 18 (8), 1622-1636 (2000).

Kreitman et al., "Phase I trial of recombinant immunotoxin RFB4(dsFv)-PE38 (BL22) in patients with B-cell malignancies," *J. Clin. Oncol.*, 23 (27), 6719-6729 (2005).

Kreitman et al., "Recombinant immunotoxins containing anti-Tac(Fv) and derivatives of *Pseudomonas* exotoxin produce complete regression in mice of an interleukin-2 receptor-expressing human carcinoma," *Blood*, 83 (2), 426-434 (1994).

Kreitman et al., "Complete regression of human B-cell lymphoma xenografts in mice treated with recombinant anti-CD22 immunotoxin RFB4(dsFv)-PE38 at doses tolerated by cynomolgus monkeys," *Int. J. Cancer*, 81 (1), 148-155 (1999).

Kuan et al., "Improved antitumor activity of a recombinant anti-Lewis(y) immunotoxin not requiring proteolytic activation," *Proc. Natl. Acad. Sci. USA*, 93 (3), 974-978 (1996).

Langer, "Polymer-controlled drug delivery systems," *Acc. Chem. Res.*, 26 (10), 537-542 (1993).

Lauwereys et al., "Potent enzyme inhibitors derived from dromedary heavy-chain antibodies," *EMBO J.*, 17 (13), 3512-3520 (1998).

Mere et al., "Acid-triggered membrane insertion of *Pseudomonas* exotoxin A involves an original mechanism based on pH-regulated tryptophan exposure," *J. Biol. Chem.*, 280 (22), 21194-21201 (2005).

Merrifield, "Solid Phase Peptide Synthesis. I. The Synthesis of a Tetrapeptide," *J. Am. Chem. Soc.*, 85, 2149-2154 (1963).

Molloy et al., "Human furin is a calcium-dependent serine endoprotease that recognizes the sequence Arg-X-X-Arg and efficiently cleaves anthrax toxin protective antigen," *J. Biol. Chem.*, 267 (23), 16396-16402 (1992).

Nakagawa et al., "Impaired invariant chain degradation and antigen presentation and diminished collagen-induced arthritis in cathepsin S null mice," *Immunity*, 10 (2), 207-217 (1999).

Narang et al., "Improved phosphotriester method for the synthesis of gene fragments," *Methods. Enzymol.*, 68, 90-98 (1979).

Needham-Vandevanter et al., "Characterization of an adduct between CC-1065 and a defined oligodeoxynucleotide duplex," *Nucl. Acids Res.*, 12 (15), 6159-6168 (1984).

Needleman et al., "A General Method Applicable to the Search for Similiarities in the Amino Acid Sequence of Two Proteins," *J. Mol. Biol.*, 48, 443-453 (1970).

Ogata et al., "Processing of *Pseudomonas* exotoxin by a cellular protease results in the generation of a 37,000-Da toxin fragment that is translocated to the cytosol," *J. Biol. Chem.*, 265 (33), 20678-20685 (1990).

Onda et al., "Inhibition of TNF-alpha produced by Kupffer cells protects against the nonspecific liver toxicity of immunotoxin anti-Tac(Fv)-PE38, LMB-2," *J. Immunol.*, 165 (12), 7150-7156 (2000).

Onda et al., "Lowering the isoelectric point of the Fv portion of recombinant immunotoxins leads to decreased nonspecific animal toxicity without affecting antitumor activity," *Cancer Res.*, 61 (13), 5070-5077 (2001).

Onda et al., "Reduction of the nonspecific animal toxicity of anti-Tac(Fv)-PE38 by mutations in the framework regions of the Fv which lower the isoelectric point," *J. Immunol.*, 163 (11), 6072-6077 (1999).

Pai et al., "Anti-tumor activities of immunotoxins made of monoclonal antibody B3 and various forms of *Pseudomonas* exotoxin," *Proc. Natl. Acad. Sci. USA*, 88 (8), 3358-3362 (1991).

(56) References Cited

OTHER PUBLICATIONS

Pastan et al., "Immunotoxin therapy of cancer," *Nat. Rev. Cancer*, 6 (7), 559-565 (2006).
Pastan et al., "Immunotoxin Treatment of Cancer," *Annu. Rev. Med.*, 58, 221-237 (2007).
Pastan et al., "Recombinant immunotoxins in the treatment of cancer," *Methods Mol. Biol.*, 248, 503-518 (2004).
Pastan, "Targeted therapy of cancer with recombinant immunotoxins," *Biochim. Biophys. Acta*, 1333 (2), C1-C6 (1997).
Pearson et al., "Improved tools for biological sequence comparison," *Proc. Natl. Acad. Sci. USA*, 85 (8), 2444-2448 (1988).
Plückthun, "Antibody engineering: advances from the use of *Escherichia coli* expression systems," *Biotechnology*, 9 (6), 545-551 (1991).
Pluger et al., "Specific role for cathepsin S in the generation of antigenic peptides in vivo," *Eur. J. Immunol.*, 32 (2), 467-476 (2002).
Prior et al., "Studies on the activity of barnase toxins in vitro and in vivo," *Bioconjug. Chem.*, 7 (1), 23-29 (1996).
Prior et al., "Translocation mediated by domain II of *Pseudomonas* exotoxin A: transport of barnase into the cytosol," *Biochemistry*, 31 (14), 3555-3559 (1992).
Reiter et al., "An antibody single-domain phage display library of a native heavy chain variable region: isolation of functional single-domain VH molecules with a unique interface," *J. Mol. Biol.*, 290 (3), 685-698 (1999).
Reiter et al., "Antitumor activity and pharmacokinetics in mice of a recombinant immunotoxin containing a disulfide-stabilized Fv fragment," *Cancer Res.*, 54 (10), 2714-2718 (1994).
Rockwell et al., "The kindest cuts of all: crystal structures of Kex2 and furin reveal secrets of precursor processing," *Trends Biochem. Sci.*, 29 (2), 80-87 (2004).
Roscoe et al., "Identification of epitopes on a mutant form of *Pseudomonas* exotoxin using serum from humans treated with *Pseudonomas* exotoxin containing immunotoxins," *Eur. J. Immunol.*, 27 (6), 1459-1468 (1997).
Salvatore et al., "Improved cytotoxic activity toward cell lines and fresh leukemia cells of a mutant anti-CD22 immunotoxin obtained by antibody phage display," *Clin. Cancer Res.*, 8 (4), 995-1002 (2002).
Saxena et al., "Formation of three-dimensional structure in proteins. I. Rapid nonenzymic reactivation of reduced lysozyme," *Biochemistry*, 9 (25), 5015-5022 (1970).
Schaub et al., "Analysis of Protein Transport to Lysosomes," *Curr. Protoc. Cell Biol.*, 15, 8.1-8.12 (2005).
Shi et al., "Cathepsin S required for normal MHC class II peptide loading and germinal center development," *Immunity*, 10 (2), 197-206 (1999).
Siegall et al., "Analysis of sequences in Domain II of *Pseudomonas* exotoxin A which mediate translocation," *Biochemistry*, 30 (29), 7154-7159 (1991).
Siegall et al., "Functional analysis of domains II, Ib, and III of *Pseudomonas* exotoxin," *J. Biol. Chem.*, 264 (24), 14256-14261 (1989).
Smith et al., "Comparison of Biosequences," *Adv. Appl. Math.*, 2, 482-489 (1981).
Taupiac et al., "A deletion within the translocation domain of *Pseudomonas* exotoxin A enhances translocation efficiency and cytotoxicity concomitantly," *Mol. Microbiology*, 31 (5), 1385-1393 (1999).
Theuer et al., "Domain II of *Pseudomonas* exotoxin A arrests the transfer of translocating nascent chains into mammalian microsomes," *Biochemistry*, 33 (19), 5890-5900 (1994).
Thomas et al., "Furin at the cutting edge: from protein traffic to embryogenesis and disease," *Nat. Rev. Mot. Cell Biol.*, 3 (10), 753-766 (2002).
Vaughan et al., "Human antibodies with sub-nanomolar affinities isolated from a large non-immunized phage display library," *Nat. Biotechnol.*, 14 (3), 309-314 (1996).
Voulhoux et al., "Influence of Deletions within Domain II of Exotoxin A on Its Extracellular Secretion from *Pseudomonas aeruginosa*," *J. Bacteriology*, 182 (14), 4051-4058 (2000).
Ward et al., "Binding activities of a repertoire of single immunoglobulin variable domain secreted from *Escherichia coli*," *Nature*, 341, 544-546 (1989).
Wedekind et al., "Refined crystallographic structure of *Pseudomonas aeruginosa* exotoxin A and its implications for the molecular mechanism of toxicity," *J. Mol. Biol.*, 314 (4), 823-837 (2001).
Yamao et al., "UGA is read as tryptophan in *Mycoplasma capricolum*," *Proc. Nat'l Acad. Sci. USA*, 82 (8), 2306-2309 (1985).
Zhang et al., "Lysosomal cathepsin B plays an important role in antigen processing, while cathepsin D is involved in degradation of the invariant chain in ovalbumin-immunized mice," *Immunology*, 100 (1), 13-20 (2000).
Weldon et al., "A Recombinant Immunotoxin Against the Tumor-Associated Antigen Mesothelin Reengineered for High Activity, Low Off-Target Toxicity, and Reduced Antigenicity," *Mol. Cancer Ther.*, 12(1): 48-57 (2012).
European Patent Office, European Search Report for European Patent Application No. 12184319.7, dated Mar. 26, 2013 (8 pages).

\* cited by examiner

|  |  | Relative Activity |
|---|---|---|
| HA22 | Fv — 251 S-----S 300 — Domain II — 350 Δ365-380 / 394 Ib Domain III | 1.00 |
| M1 | Fv ---- 274 — 394 Domain III | 1.43 |
| M2 | Fv 251 — 364 ---- Domain III | 0.78 |
| M3 | Fv ---- 274 C287S 349 ---- Domain III | 1.64 |
| M4 | Fv ---- 281 C287S 348 ---- Domain III | 0.22 |
| M5 (HA22-LR) | Fv ---- 274 284 ---- Domain III  RHRQPR↓GWEQL | 0.49 |

*FIG. 3*

[Immunotoxin] (ng/ml)

$t_{1/2}$ = 14.6 min $t_{1/2}$ = 7.8 min

Time (minutes)

FIG. 5

SEQUENCE LISTING

<160> NUMBER OF SEQ ID NOS: 34

<210> SEQ ID NO 1
<211> LENGTH: 613
<212> TYPE: PRT
<213> ORGANISM: Pseudomonas aeruginosa
<220> FEATURE:
<223> OTHER INFORMATION: native Pseudomonas exotoxin A (PE)

<400> SEQUENCE: 1

```
Ala Glu Glu Ala Phe Asp Leu Trp Asn Glu Cys Ala Lys Ala Cys Val
 1               5                  10                  15

Leu Asp Leu Lys Asp Gly Val Arg Ser Ser Arg Met Ser Val Asp Pro
             20                  25                  30

Ala Ile Ala Asp Thr Asn Gly Gln Gly Val Leu His Tyr Ser Met Val
         35                  40                  45

Leu Glu Gly Gly Asn Asp Ala Leu Lys Leu Ala Ile Asp Asn Ala Leu
     50                  55                  60

Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
                 85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350
```

```
Gln Gly Thr Gly Asn Asp Glu Ala Gly Ala Ala Asn Ala Asp Val Val
            355                 360                 365

Ser Leu Thr Cys Pro Val Ala Ala Gly Glu Cys Ala Gly Pro Ala Asp
        370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 2
<211> LENGTH: 4
<212> TYPE: PRT
<213> ORGANISM: Artificial Sequence
<220> FEATURE:
<223> OTHER INFORMATION: synthetic PE carboxyl terminus additional
      sequence

<400> SEQUENCE: 2

Lys Asp Glu Leu
 1

<210> SEQ ID NO 3
<211> LENGTH: 4
<212> TYPE: PRT
<213> ORGANISM: Artificial Sequence
<220> FEATURE:
<223> OTHER INFORMATION: synthetic PE carboxyl terminus additional
      sequence

<400> SEQUENCE: 3

Arg Glu Asp Leu
 1
```

```
<210> SEQ ID NO 4
<211> LENGTH: 128
<212> TYPE: PRT
<213> ORGANISM: Artificial Sequence
<220> FEATURE:
<223> OTHER INFORMATION: synthetic 38 kD PE truncated form (PE38)
      domains II (residues 251-364) and Ib
      (residues 365-394)

<400> SEQUENCE: 4
```

Pro Glu Gly Gly Ser Leu Ala Ala Leu Thr Ala His Gln Ala Cys His
 1               5                  10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Asn Gly Pro Ala Asp Ser Gly Asp Ala Leu Leu Glu Arg Asn Tyr
        115                 120                 125

```
<210> SEQ ID NO 5
<211> LENGTH: 5
<212> TYPE: PRT
<213> ORGANISM: Artificial Sequence
<220> FEATURE:
<223> OTHER INFORMATION: synthetic native PE carboxyl terminal sequence
      (residues 609-613)

<400> SEQUENCE: 5
```

Arg Glu Asp Leu Lys
 1               5

```
<210> SEQ ID NO 6
<211> LENGTH: 4
<212> TYPE: PRT
<213> ORGANISM: Artificial Sequence
<220> FEATURE:
<223> OTHER INFORMATION: synthetic minimal furin cleavage site
<220> FEATURE:
<221> NAME/KEY: MOD_RES
<222> LOCATION: (2)...(3)
<223> OTHER INFORMATION: Xaa = any amino acid

<400> SEQUENCE: 6
```

Arg Xaa Xaa Arg
 1

```
<210> SEQ ID NO 7
<211> LENGTH: 4
<212> TYPE: PRT
<213> ORGANISM: Artificial Sequence
<220> FEATURE:
<223> OTHER INFORMATION: synthetic furin cleavage site, cleavage motif
      consensus sequence
<220> FEATURE:
<221> NAME/KEY: MOD_RES
<222> LOCATION: (2)...(2)
<223> OTHER INFORMATION: Xaa = any amino acid
```

```
<220> FEATURE:
<221> NAME/KEY: MOD_RES
<222> LOCATION: (3)...(3)
<223> OTHER INFORMATION: Xaa = Arg or Lys

<400> SEQUENCE: 7

Arg Xaa Xaa Arg
 1

<210> SEQ ID NO 8
<211> LENGTH: 4
<212> TYPE: PRT
<213> ORGANISM: Artificial Sequence
<220> FEATURE:
<223> OTHER INFORMATION: synthetic furin cleavage site
<220> FEATURE:
<221> NAME/KEY: MOD_RES
<222> LOCATION: (2)...(2)
<223> OTHER INFORMATION: Xaa =  any amino acid

<400> SEQUENCE: 8

Arg Xaa Arg Arg
 1

<210> SEQ ID NO 9
<211> LENGTH: 4
<212> TYPE: PRT
<213> ORGANISM: Artificial Sequence
<220> FEATURE:
<223> OTHER INFORMATION: synthetic furin cleavage site
<220> FEATURE:
<221> NAME/KEY: MOD_RES
<222> LOCATION: (2)...(2)
<223> OTHER INFORMATION: Xaa = any amino acid

<400> SEQUENCE: 9

Arg Xaa Lys Arg
 1

<210> SEQ ID NO 10
<211> LENGTH: 11
<212> TYPE: PRT
<213> ORGANISM: Artificial Sequence
<220> FEATURE:
<223> OTHER INFORMATION: synthetic native furin cleavage sequence (FCS)
      in domain II of PE

<400> SEQUENCE: 10

Arg His Arg Gln Pro Arg Gly Trp Glu Gln Leu
 1               5                   10

<210> SEQ ID NO 11
<211> LENGTH: 11
<212> TYPE: PRT
<213> ORGANISM: Artificial Sequence
<220> FEATURE:
<223> OTHER INFORMATION: synthetic furin cleavable sequence with
      substitutions at positions P3 and P2

<400> SEQUENCE: 11

Arg His Arg Ser Lys Arg Gly Trp Glu Gln Leu
 1               5                   10

<210> SEQ ID NO 12
<211> LENGTH: 4
<212> TYPE: PRT
<213> ORGANISM: Artificial Sequence
<220> FEATURE:
<223> OTHER INFORMATION: synthetic furin cleavage sequence (FCS)
```

```
<400> SEQUENCE: 12

Arg Lys Lys Arg
 1

<210> SEQ ID NO 13
<211> LENGTH: 4
<212> TYPE: PRT
<213> ORGANISM: Artificial Sequence
<220> FEATURE:
<223> OTHER INFORMATION: synthetic furin cleavage sequence (FCS)

<400> SEQUENCE: 13

Arg Arg Arg Arg
 1

<210> SEQ ID NO 14
<211> LENGTH: 4
<212> TYPE: PRT
<213> ORGANISM: Artificial Sequence
<220> FEATURE:
<223> OTHER INFORMATION: synthetic furin cleavage sequence (FCS)

<400> SEQUENCE: 14

Arg Lys Ala Arg
 1

<210> SEQ ID NO 15
<211> LENGTH: 6
<212> TYPE: PRT
<213> ORGANISM: Artificial Sequence
<220> FEATURE:
<223> OTHER INFORMATION: synthetic furin cleavage sequence (FCS)

<400> SEQUENCE: 15

Ser Arg Val Ala Arg Ser
 1               5

<210> SEQ ID NO 16
<211> LENGTH: 9
<212> TYPE: PRT
<213> ORGANISM: Artificial Sequence
<220> FEATURE:
<223> OTHER INFORMATION: synthetic furin cleavage sequence (FCS)

<400> SEQUENCE: 16

Thr Ser Ser Arg Lys Arg Arg Phe Trp
 1               5

<210> SEQ ID NO 17
<211> LENGTH: 9
<212> TYPE: PRT
<213> ORGANISM: Artificial Sequence
<220> FEATURE:
<223> OTHER INFORMATION: synthetic furin cleavage sequence (FCS)

<400> SEQUENCE: 17

Ala Ser Arg Arg Lys Ala Arg Ser Trp
 1               5

<210> SEQ ID NO 18
<211> LENGTH: 8
<212> TYPE: PRT
<213> ORGANISM: Artificial Sequence
<220> FEATURE:
<223> OTHER INFORMATION: synthetic furin cleavable sequence
```

<400> SEQUENCE: 18

Arg Arg Val Lys Lys Arg Phe Trp
1 5

<210> SEQ ID NO 19
<211> LENGTH: 8
<212> TYPE: PRT
<213> ORGANISM: Artificial Sequence
<220> FEATURE:
<223> OTHER INFORMATION: synthetic furin cleavable sequence

<400> SEQUENCE: 19

Arg Asn Val Val Arg Arg Asp Trp
1 5

<210> SEQ ID NO 20
<211> LENGTH: 9
<212> TYPE: PRT
<213> ORGANISM: Artificial Sequence
<220> FEATURE:
<223> OTHER INFORMATION: synthetic furin cleavable sequence

<400> SEQUENCE: 20

Thr Arg Ala Val Arg Arg Arg Ser Trp
1 5

<210> SEQ ID NO 21
<211> LENGTH: 4
<212> TYPE: PRT
<213> ORGANISM: Artificial Sequence
<220> FEATURE:
<223> OTHER INFORMATION: synthetic furin cleavable sequence

<400> SEQUENCE: 21

Arg Gln Pro Arg
1

<210> SEQ ID NO 22
<211> LENGTH: 8
<212> TYPE: PRT
<213> ORGANISM: Artificial Sequence
<220> FEATURE:
<223> OTHER INFORMATION: synthetic furin cleavable sequence

<400> SEQUENCE: 22

Arg His Arg Gln Pro Arg Gly Trp
1 5

<210> SEQ ID NO 23
<211> LENGTH: 9
<212> TYPE: PRT
<213> ORGANISM: Artificial Sequence
<220> FEATURE:
<223> OTHER INFORMATION: synthetic furin cleavable sequence

<400> SEQUENCE: 23

Arg His Arg Gln Pro Arg Gly Trp Glu
1 5

<210> SEQ ID NO 24
<211> LENGTH: 9
<212> TYPE: PRT
<213> ORGANISM: Artificial Sequence
<220> FEATURE:
<223> OTHER INFORMATION: synthetic furin cleavable sequence

```
<400> SEQUENCE: 24

His Arg Gln Pro Arg Gly Trp Glu Gln
1               5

<210> SEQ ID NO 25
<211> LENGTH: 7
<212> TYPE: PRT
<213> ORGANISM: Artificial Sequence
<220> FEATURE:
<223> OTHER INFORMATION: synthetic furin cleavable sequence

<400> SEQUENCE: 25

Arg Gln Pro Arg Gly Trp Glu
1               5

<210> SEQ ID NO 26
<211> LENGTH: 4
<212> TYPE: PRT
<213> ORGANISM: Artificial Sequence
<220> FEATURE:
<223> OTHER INFORMATION: synthetic furin cleavable sequence

<400> SEQUENCE: 26

Arg Ser Lys Arg
1

<210> SEQ ID NO 27
<211> LENGTH: 8
<212> TYPE: PRT
<213> ORGANISM: Artificial Sequence
<220> FEATURE:
<223> OTHER INFORMATION: synthetic furin cleavable sequence

<400> SEQUENCE: 27

Arg His Arg Ser Lys Arg Gly Trp
1               5

<210> SEQ ID NO 28
<211> LENGTH: 8
<212> TYPE: PRT
<213> ORGANISM: Artificial Sequence
<220> FEATURE:
<223> OTHER INFORMATION: synthetic furin cleavable sequence

<400> SEQUENCE: 28

His Arg Ser Lys Arg Gly Trp Glu
1               5

<210> SEQ ID NO 29
<211> LENGTH: 9
<212> TYPE: PRT
<213> ORGANISM: Artificial Sequence
<220> FEATURE:
<223> OTHER INFORMATION: synthetic furin cleavable sequence

<400> SEQUENCE: 29

Arg Ser Lys Arg Gly Trp Glu Gln Leu
1               5

<210> SEQ ID NO 30
<211> LENGTH: 10
<212> TYPE: PRT
<213> ORGANISM: Artificial Sequence
<220> FEATURE:
<223> OTHER INFORMATION: synthetic furin cleavable sequence
```

```
<400> SEQUENCE: 30

His Arg Ser Lys Arg Gly Trp Glu Gln Leu
 1               5                  10

<210> SEQ ID NO 31
<211> LENGTH: 6
<212> TYPE: PRT
<213> ORGANISM: Artificial Sequence
<220> FEATURE:
<223> OTHER INFORMATION: synthetic furin cleavable sequence

<400> SEQUENCE: 31

Arg His Arg Ser Lys Arg
 1               5

<210> SEQ ID NO 32
<211> LENGTH: 4
<212> TYPE: PRT
<213> ORGANISM: Artificial Sequence
<220> FEATURE:
<223> OTHER INFORMATION: synthetic mutated terminal residues of PE
      (residues 609-613)

<400> SEQUENCE: 32

Arg Glu Glu Leu
 1

<210> SEQ ID NO 33
<211> LENGTH: 4
<212> TYPE: DNA
<213> ORGANISM: Artificial Sequence
<220> FEATURE:
<223> OTHER INFORMATION: synthetic tetranucleotide consensus "hotspot
      motif" sequence

<400> SEQUENCE: 33 rgyw                                                                       4

<210> SEQ ID NO 34
<211> LENGTH: 3
<212> TYPE: DNA
<213> ORGANISM: Artificial Sequence
<220> FEATURE:
<223> OTHER INFORMATION: synthetic serine consensus "hotspot motif"
      sequence

<400> SEQUENCE: 34 agy                                                                        3
```

DELETIONS IN DOMAIN II OF PSEUDOMONAS EXOTOXIN A THAT REMOVE IMMUNOGENIC EPITOPES

CROSS-REFERENCES TO RELATED APPLICATIONS

This application is a U.S. National Stage Application of PCT/US2008/075296, filed Sep. 4, 2008, which claims priority to and benefit of U.S. Provisional Application 60/969,929, filed Sep. 4, 2007, and U.S. Provisional Application 61/018,853, filed Jan. 3, 2008, the contents of which are incorporated herein for all purposes.

STATEMENT AS TO RIGHTS TO INVENTIONS MADE UNDER FEDERALLY SPONSORED RESEARCH AND DEVELOPMENT

Not Applicable.

REFERENCE TO A "SEQUENCE LISTING," A TABLE, OR A COMPUTER PROGRAM LISTING APPENDIX SUBMITTED AS AN ASCII TEXT FILE

The Sequence Listing written in file—545-1.TXT, created on May 15, 2012, 16,384 bytes, machine format IBM-PC, MS-Windows operating system, is hereby incorporated by reference in its entirety for all purposes.

BACKGROUND OF THE INVENTION

In the past several years immunoconjugates have been developed as an alternative therapeutic approach to treat malignancies. Immunoconjugates were originally composed of an antibody chemically conjugated to a plant or a bacterial toxin, a form that is known as an immunotoxin. The antibody binds to the antigen expressed on the target cell and the toxin is internalized causing cell death by arresting protein synthesis and inducing apoptosis (Brinkmann, U., *Mol. Med. Today,* 2:439-446 (1996)). More recently, genes encoding the antibody and the toxin have been fused and the immunotoxin expressed as a fusion protein.

A variety of plant, fungal, and bacterial toxins have been adapted for use with immunotoxins, including ricin, diphtheria toxin, and *Pseudomonas* exotoxin A (PE) (Pastan, I. et al., *Nat Rev Cancer,* 6:559-565 (2006); Pastan, I. et al., *Annu Rev Med,* 58:221-237 (2007)). PE-based immunotoxins are currently in clinical trials for the treatment of CD22-expressing lymphomas and leukemias, as well as mesothelin-expressing solid tumors (Kreitman, R., et al., *J Clin Oncol,* 23:6719-6729 (2005); Hassan, R., *Clin Cancer Res,* 13:5144-5149 (2007)). Typically, the PE has been truncated or mutated to reduce its non-specific toxicity while retaining its toxicity to cells to which it is targeted by the targeting portion of the immunotoxin. Over the years, numerous mutated and truncated forms of PE have been developed. The one used in most clinical trials to date is a 38 kD truncated form referred to as "PE38."

Despite these decades of efforts, current PE-based immunotoxins are still not fully satisfactory. Although the PE38 immunotoxins that have reached clinical trials are comparatively well tolerated at low doses, dose-limiting toxicities have restricted their therapeutic effect. In a phase I clinical trial of a PE-based immunotoxin known as LMB-2, dose-limiting toxicities above 40 µg/kg given every other day (QOD) X 3 consisted of transaminase elevation, diarrhea, cardiomyopathy and an allergic reaction (Kreitman, R. J. et al., *J Clin Oncol,* 18:1622-1636 (2000)). In a phase I clinical trial of an anti-mesothelin immunotoxin, referred to as SS1P, adverse events of pleuritis, urticaria, and vascular leak syndrome were found to be dose limiting (Hassan, R. et al., *Clin Cancer Res,* 13:5144-5149 (2007)). In a phase I trial of a third PE-based immunotoxin, BL22, dose-limiting toxicities included several cases of hemolytic uremic syndrome and a cytokine release syndrome with systemic vascular leak syndrome (Kreitman, R. J. et al., *J Clin Oncol,* 23:6719-6729 (2005)).

Further, the PE-based immunotoxins currently in clinical trials are highly immunogenic. This has proven not to be a problem in the treatment of hematological malignancies, in which the ability of the immune system to mount a response is often compromised. Immunotoxins can typically be administered multiple times to patients with hematological malignancies. Patients with solid tumors, however, usually develop neutralizing antibodies to PE-based immunotoxins within weeks after the first administration. Since many protocols call for a three week period between administration of immunotoxins, the development of the antibodies during this period effectively means that, for solid tumors, usually only one administration can be made of a PE-based immunotoxin before the patient's antibodies render it ineffective. Even a single administration of a PE-based immunotoxin can be highly useful in reducing the patient's tumor burden, in eliminating smaller metastases, and in alleviating symptoms, but the ability to administer multiple doses would clearly be useful.

A limited number of approaches have been developed as an attempt to address these problems. One approach to reducing non-specific toxicity, reducing the isoelectric point of the framework regions of Fvs used as the targeting moiety of immunotoxins, was reported in co-owned PCT Application No. PCT/US01/43602, published as International Publication No. WO 02/40545. An approach to reducing immunogenicity is described in co-owned PCT application No. PCT/US06/028986, published as WO 2007/016150, which reports mapping of the various epitopes of PE and mutations of individual amino acid residues that could be combined to reduce the overall immunogenicity of the resulting PE molecule compared to that of PE38. Nonetheless, it would be desirable to have additional approaches of reducing the dose-limiting toxicity of the immunotoxin. Further, it would be desirable to have additional approaches for reducing the immunogenicity of PE and of immunotoxins in which PE acts as the toxic moiety. The present invention satisfies these and other needs.

BRIEF SUMMARY OF THE INVENTION

In a first group of embodiments, the invention provides isolated, mutated *Pseudomonas* exotoxin As ("PE"s), comprising a sequence of the following formula:

$$R^1_n\text{-FCS-}R^2_n\text{-}R^3_n\text{-PE functional domain III},$$

wherein:
n=0 or 1
$R^1$=1 to 10 amino acid residues
FCS=a furin cleavage sequence of amino acid residues, which sequence is cleavable by furin and has an amino end and a carboxyl end,
$R^2$=1 to 10 amino acid residues;
$R^3$=1 or more contiguous residues of residues 365-394 of SEQ ID NO:1; and, PE functional domain III=residues 395-613 of SEQ ID NO:1, optionally comprising (i) substitutions in one or more residues corresponding to 609-613 of SEQ ID NO:1, (ii) a substitution of glycine, alanine, valine, leucine, or isoleucine for arginine at a position corresponding to position 490 of SEQ ID NO:1, (iii) a substitution of one or more residues corresponding to residues of SEQ ID NO:1, which residues of SEQ ID NO:1 maintain immunogenicity of a epitope or subepitope of PE domain III, or (iv) a combination of any of (i)-(iii). In some embodiments, the FCS is represented by the formula P4-P3-P2-P1, wherein P4 is an amino acid residue at the amino end, P1 is an amino acid residue at the carboxyl end, P1 is an arginine or a lysine residue, and said sequence is cleavable at the carboxyl end of P1 by furin. In some embodiments, the FCS (i) further comprises amino acid residues represented by P6-P5 at said amino end, (ii) further comprises amino acid residues represented by P1'-P2' at said carboxyl end, (iii) further wherein P1 is an arginine or a lysine residue, P2' is tryptophan, and P4 can be arginine, valine or lysine, provided that if P4 is not arginine, then P6 and P2 are basic residues, and (iv) said sequence is cleavable at the carboxyl end of P1 by furin. In some embodiments, the FCS is SEQ ID NO:10. In some embodiments, the PE functional domain III consists of the sequence of residues 395 to 613 of SEQ ID NO:1. In some embodiments, the mutated PE comprises one or more contiguous residues of residues 365-394 of SEQ ID NO:1 between the FCS and the PE functional domain III. In some embodiments, "n" is 0 for R1, R2, and R3.

In a further group of embodiments, the invention provides chimeric molecules comprising (a) a ligand, which ligand specifically binds to an antigen or receptor on a cell surface, conjugated or fused to (b) a mutated *Pseudomonas* exotoxin A (PE) comprising a sequence of the following formula:

$$R^1_n\text{-FCS-}R^2_n\text{-}R^3_n\text{-PE functional domain III},$$

wherein:
n=0 or 1 independently for each of $R^1$, $R^2$ and $R^3$,
$R^1$=1 to 10 amino acid residues
FCS=a furin cleavage sequence of amino acid residues, which sequence is cleavable by furin and has an amino end and a carboxyl end,
$R^2$=1 to 10 amino acid residues;
$R^3$=1 or more contiguous residues of residues 365-394 of SEQ ID NO:1; and,
PE functional domain III=residues 395-613 of SEQ ID NO:1, optionally comprising (i) substitutions in one or more residues corresponding to 609-613 of SEQ ID NO:1, (ii) a substitution of glycine, alanine, valine, leucine, or isoleucine for arginine at a position corresponding to position 490 of SEQ ID NO:1, (iii) a substitution of one or more residues corresponding to residues of SEQ ID NO:1, which residues of SEQ ID NO:1 maintain immunogenicity of a epitope or subepitope of PE domain III, or (iv) a combination of any of (i)-(iii), and wherein said ligand is not transforming growth factor α. In some embodiments, the FCS can be represented by the formula P4-P3-P2-P1 (SEQ ID NO:36), wherein P4 designates the amino end, P1 designates the carboxyl end, P1 is an arginine residue, and the sequence is cleavable on the carboxyl end of P1 by furin. In some embodiments, the FCS (i) further comprises amino acid residues represented by P6-P5 on said amino end, (ii) further comprises amino acid residues represented by P1'-P2' on said carboxyl end, (iii) further wherein P1 is an arginine residue, P2' is tryptophan, and P4 can be arginine, valine or lysine, provided that if P4 is not arginine, then P6 and P2 are basic residues, and (iv) said sequence is cleavable on the carboxyl end of P1 by furin. In some embodiments, the FCS is SEQ ID NO:10. In some embodiments, the PE functional domain III consists of the sequence of residues 395 to 613 of SEQ ID NO:1. In some embodiments, the mutated PE comprises one or more contiguous residues of residues 365-394 of SEQ ID NO:1 between said FCS and said PE domain III. In some embodiments, "n" is 0 for R1, R2, and R3. In some embodiments, the ligand is an antibody or fragment thereof which retains antigen recognition capability.

In yet a further group of embodiments, the invention provides methods of inhibiting the growth of target cells having an exterior. The methods comprise contacting the cells with chimeric molecules, which comprise (a) a ligand which specifically binds to an antigen or receptor on the exterior of the cells, which ligand is conjugated or fused to (b) a mutated *Pseudomonas* exotoxin A (PE) comprising a sequence of the following formula:

$$R^1_n\text{-FCS-}R^2_n\text{-}R^3_n\text{-PE functional domain III},$$

wherein:
n=0 or 1 independently for each of $R^1$, $R^2$ and $R^3$,
$R^1$=1 to 10 amino acid residues
FCS=a furin cleavage sequence of amino acid residues, which sequence is cleavable by furin and has an amino end and a carboxyl end,
$R^2$=1 to 10 amino acid residues;
$R^3$=1 or more contiguous residues of residues 365-394 of SEQ ID NO:1; and,
PE functional domain III=residues 395-613 of SEQ ID NO:1, optionally comprising (i) substitutions in one or more residues corresponding to 609-613 of SEQ ID NO:1, (ii) a substitution of glycine, alanine, valine, leucine, or isoleucine for arginine at a position corresponding to position 490 of SEQ ID NO:1, (iii) a substitution of one or more residues corresponding to residues of SEQ ID NO:1, which residues of SEQ ID NO:1 maintain immunogenicity of a epitope or subepitope of PE functional domain III, or (iv) a combination of any of (i)-(iii), and further wherein said ligand is not transforming growth factor α, and wherein contacting of said chimeric molecule to said cell inhibits the growth of said cell. In some embodiments, the FCS can be represented by the formula P4-P3-P2-P1, wherein P4 designates the amino end, P1 designates the carboxyl end, P1 is an arginine residue, and said sequence is cleavable on the carboxyl end of P1 by furin. In some embodiments, the FCS (i) further comprises amino acid residues represented by P6-P5 on said amino end, (ii) further comprises amino acid residues represented by P1'-P2' on said carboxyl end, (iii) further wherein P1 is an arginine residue, P2' is tryptophan, and P4 can be arginine, valine or lysine, provided that if P4 is not arginine, then P6 and P2 are basic residues, and (iv) said sequence is cleavable at the carboxyl end of P1 by furin. In some embodiments, the FCS is SEQ ID NO:10. In some embodiments, the PE functional domain III consists of the sequence of residues 395 to 613 of SEQ ID NO:1. In some embodiments, the mutated PE comprises one or more contiguous residues of residues 365-394 of SEQ ID NO:1 between said FCS and said PE domain III. In some embodiments, the ligand is an antibody or fragment thereof which retains antigen recognition capability.

In yet a further group of embodiments, the invention provides nucleic acids encoding the mutated PEs and chimeric molecules described above. In particular, the invention provides isolated nucleic acids encoding mutated *Pseudomonas* exotoxin As (PEs), comprising a sequence of the following formula:
$R^1_n$-FCS-$R^2_n$-$R^3_n$-PE functional domain III wherein:

n=0 or 1 independently for each of $R^1$, $R^2$ and $R^3$, $R^1$=1 to 10 amino acid residues FCS=a furin cleavage sequence of amino acid residues, which sequence is cleavable by furin and has an amino end and a carboxyl end, $R^2$=1 to 10 amino acid residues;

$R^3$=1 or more contiguous residues of residues 365-394 of SEQ ID NO:1; and,

PE functional domain III=residues 395-613 of SEQ ID NO:1, optionally comprising (i) substitutions in one or more residues corresponding to 609-613 of SEQ ID NO:1, (ii) a substitution of glycine, alanine, valine, leucine, or isoleucine for arginine at a position corresponding to position 490 of SEQ ID NO:1, (iii) a substitution of one or more residues corresponding to residues of SEQ ID NO:1, which residues of SEQ ID NO:1 maintain immunogenicity of a epitope or subepitope of PE domain III, or (iv) a combination of any of (i)-(iii). In some embodiments, the FCS can be represented by the formula P4-P3-P2-P1, wherein P4 designates the amino end, P1 designates the carboxyl end, P1 is an arginine residue, and said sequence is cleavable on the carboxyl end of P1 by furin. In some embodiments, the FCS (i) further comprises amino acid residues represented by P6 P5 on said amino end, (ii) further comprises amino acid residues represented by P1' P2' on said carboxyl end, (iii) further wherein P1 is an arginine residue, P2' is tryptophan, and P4 can be arginine, valine or lysine, provided that if P4 is not arginine, then P6 and P2 are basic residues, and (iv) said sequence is cleavable at the carboxyl end of P1 by furin. In some embodiments, the FCS is SEQ ID NO:10. In some embodiments, the PE domain III consists of the sequence of residues 395 to 613 of SEQ ID NO:1. In some embodiments, the nucleic acid further encodes a ligand which specifically binds to an antigen or receptor on a cell surface, which ligand is fused directly or through a peptide linker to said PE. In some embodiments, the ligand is an antibody or portion thereof which retains antigen binding capability.

BRIEF DESCRIPTION OF THE DRAWINGS

FIGS. 1A and 1B. FIG. 1A is a schematic of the structure of the anti-CD22 immunotoxin known as "HA22". HA22 comprises a disulfide-linked Fv (VH/VL) anti-CD22 antibody fragment recombinantly connected to a 38 kD cytotoxic truncation of *Pseudomonas* exotoxin A ("PE", the 38 kD truncation is known in the art as "PE38"). PE38 is created by deleting from the 613 amino acid residue sequence of native PE residues 1-252, which correspond to domain I, along with residues 365-380 of domain Ib. FIG. 1B shows the sequence of PE38 domains II (residues 251-364) and Ib (residues 365-394) (SEQ ID NO:4). Residue numbering is based on the amino acid sequence of native PE. Residues 365 to 380 from native PE (boxed) were deleted in the generation of PE38. Lysosomal protease cleavage sites are indicated by arrows adjacent to the designation of their corresponding band from SDS-PAGE analysis. Lysosomal protease cleavage sites occur between residues 260-261, 265-266, 297-298, 341-342, 342-343, 351-352, 352-353, 353-354, 364-381, 390-391, and 391-392. The furin cleavage site (279-280) is also indicated. The 11-residue furin-sensitive sequence in domain II from HA22-LR is shaded.

FIG. 2. FIG. 2 is a schematic of the structure of HA22 mutant "JW008". JW008 is a form of HA22 which has the same truncations of PE38 as HA22 LR, but in which the native sequence of the furin cleavable sequence of residues 274-284 has been altered by substitutions of two residues (SEQ ID NO:11).

FIG. 3. FIG. 3 shows schematic drawings of HA22 and of a series of variants in which deletions were introduced into domains II and Ib of the PE38 component of HA22 to eliminate lysosomal protease cleavage sites. These five mutant proteins (M1, M2, M3, M4, and M5) are illustrated using an expanded view of domains II and Ib of PE38 to show the extent of the deletions (dotted lines) and the presence in M3 and M4 of a C287S point mutation. Residue numbering is based on the location of amino acids in native PE. The proteins were subsequently purified and compared to HA22 using an in vitro cytotoxicity assay on Raji cells. The M5 protein is also referred to herein as "HA22-LR" (SEQ ID NO:10). The $IC_{50}$ (ng/ml) of each mutant relative to the $IC_{50}$ of HA22 is presented as a mean of at least three separate experiments.

FIG. 4. HA22-LR is resistant to digestion with lysosomal extracts. HA22 and HA22-LR were incubated with lysosomal extracts of Raji cells under identical conditions. Following the addition of lysosomal extract, samples were removed immediately (O), after 30 min, and after 1, 2, 4, 8, and 24 h, then analyzed by reducing SDS-PAGE. Arrows indicate the $V_L$, $V_H$-PE38 (HA22), and $V_H$-PE25 (HA22-LR) bands that comprise the mature immunotoxins.

FIG. 5. Pharmacokinetics of HA22-LR. Balb/C mice were injected intravenously with 10 μg of either HA22 (□) or HA22-LR (○) and bled at several intervals between 2 and 60 min from the time of injection. The concentration of immunotoxin in the serum at the various intervals was determined by ELISA and fit to a single exponential decay function. The corresponding half-life ($t_{1/2}$) is indicated. Each point is the concentration of immunotoxin in the serum of one mouse, and the concentration at each time interval was determined from at least two different mice.

FIG. 6. HA22-LR has potent antitumor activity. SCID mice with CA46 xenograft tumors were treated QDD X 3 (on days 6, 8, and 10) intravenously with PBS (x; solid line), 0.3 mg/kg HA22 (○; solid line), or HA22-LR at 1.0 (▲; dashed line), 1.75 (□; solid line), or 2.5 (*; dashed line) mg/kg. Arrows indicate days when treatment was administered. Tumor size was measured over the course of 40 days. Points represent the mean tumor size of all mice in the treatment group. Error bars show the 95% confidence interval of each mean value.

DETAILED DESCRIPTION OF THE INVENTION

Introduction

For the past twenty years, *Pseudomonas* exotoxin A ("PE") has been intensively studied for use as the toxic portion of targeted toxins, such as immunotoxins. The most common form of PE used in targeted toxins has been a 38 kD form known as PE38, in which the entirety of domain I of the toxin has been deleted, along with residues 365-379 of domain Ib. PE38 contains the entirety of domains II and III of the toxin. Domain II of PE has a sequence recognized and cleaved by an enzyme known as furin, which is present in animal cells. PEs containing the furin cleavage sequence undergo proteolytic processing inside target cells, activating the cytotoxic activity of the toxin. Some forms of PE developed in the past attempted to increase activity by eliminating the portion of domain II upstream of the furin cleavage site, in the hope that this would eliminate the need for proteolytic processing inside target cells.

Surprisingly, we have now discovered that forms of PE can be made by reversing some of the strategies previously used to develop PEs for use in targeted toxins, and that these new forms of PE have advantages not provided by previous PEs. Further surprisingly, these new forms of PE retain excellent cytotoxic activity and are much less non-specific toxicity in in vivo use. This decrease in toxicity allows much higher doses to be given, with a concomitant increase in anti-tumor activity.

In the new forms of PE, we have deleted the remaining residues of domain Ib (other than those needed for good ADP-ribosylation activity), which were thought to be useful in facilitating effective translocation of the toxin in the target cell following proteolytic activation. Second, we have deleted all of domain II except for the furin cleavage sequence.

The elimination of most of domain II and all of domain Ib provides PE molecules with a number of advantages over the forms of PE previously available. First, both domain Ib and domain II contain epitopes that add to the overall immunogenicity of PE. By eliminating all of domain II except for the furin cleavage site and the portion of domain Ib previously included even in truncated PEs, both linear and conformational epitopes present in the domains are eliminated, reducing the immunogenicity of the resulting PE compared to the forms of the toxin that have previously been available.

Second, the overall size of the toxin is reduced. The exemplar forms studied in the course of the present work had a molecular weight of 25 kD, and therefore represent a decrease of some 13 kD from the size of the most common form of PE currently in use, PE38. Smaller molecules may be able to penetrate more deeply into solid tumors, and it has therefore generally been deemed desirable to develop smaller forms of the toxin for use against solid tumors. The smaller size of the PEs of the invention compared to those previously available suggest that they will prove useful both in the treatment of solid tumors, in which the smaller size of the toxin may facilitate tumor penetration, and in treating hematological malignancies, in which the size of the toxin is of less importance. Further, PEs are used as the toxic moieties of toxins directed to target cells other than tumor cells. The smaller toxins of the invention should be useful in the context of these target cells as well.

Third, and surprisingly, in vivo tests showed that immunotoxins made with the resulting toxins retained good cytotoxicity to most target cells, while having markedly less non-specific toxicity in an animal model than did the comparable immunotoxin made with PE38. In fact, while mice bearing xenograft tumors of a human hematological malignancy showed a complete response when injected with the immunotoxin multiple times at 2.5 mg/kg, no mice died when injected with the immunotoxin multiple times at 5.0 mg/kg (the equivalent of 100 mg per dose). In comparison, the LD50 of HA22 in mice is approximately 1.3 mg/kg. These results show not only that mice can tolerate doses of the new immunotoxins more than 3 times that of a like immunotoxin made with PE38, but they can tolerate doses at least twice that needed to induce a complete response.

Fourth, some previous forms of PE in which a portion of domain II was deleted eliminated the furin cleavage site. This eliminated the need for intracellular cleavage by furin, but also made it harder to engineer a functional molecule. Typically, the antibody was attached to PE domain III, and tended to remain associated with the PE moiety within the cell. In chimeric molecules using PEs of the present invention, the antibody or other targeting moiety can be attached upstream of the furin cleavage site and be cleaved away from PE domain III once inside the cell.

Both in vitro and in vivo studies were conducted on an exemplar PE of the invention to compare its effects when made into an immunotoxin to those of a like immunotoxin made with PE38. The exemplar immunotoxin chosen for comparison is an immunotoxin known as HA22, which employs an anti-CD22 antibody fused to PE38. Comparisons were made between an immunotoxin in which the antibody used in HA22 was fused to one of the new PEs as the toxin (for convenience, this construct will be referred to as "HA22-LR", with the "LR" referring to resistance of the modified PE component to lysosomal degradation) to HA22 (in which the same antibody is fused to PE38). In in vitro studies, the immunotoxin made with the new PE had approximately the same cytotoxicity as HA22 against cells of various cell lines that express CD22. In in vivo studies in an animal model, the HA22-LR immunotoxin was estimated to be less cytotoxic than HA22, the immunotoxin made with PE38. The new immunotoxin, however, also had significantly reduced non-specific toxicity, and could be tolerated by the mice at much higher doses than HA22, thereby enhancing the anti-tumor effect of the treatment and permitting a larger therapeutic window between the maximum tolerated dose and that needed to induce a complete response.

A number of immunotoxins have been made using different antibodies or other ligands as the targeting moiety, but using a PE as the toxin moiety. It has been known that, in some instances, the targeting moiety can make some contribution to the non-specific toxicity of an immunotoxin. See, e.g., co-owned PCT Application No. PCT/US01/43602, published as International Publication No. WO 02/40545, which reports that non-specific toxicity of some immunotoxins could be reduced by reducing the isoelectric point of the framework regions of Fvs used as the targeting moiety. It has also become clear, however, that, in immunotoxins and other chimeric molecules using PE as the toxin moiety, the major contributor to non-specific toxicity is the PE component. Thus, it is expected that reduced non-specific toxicity similar to that observed with respect to the HA22-LR immunotoxin in the studies reported herein will also result when the PEs of the invention are used as the toxin moiety of chimeric molecules using as the targeting moiety antibodies other than the antibody used in HA22 as the targeting moiety or other ligands as the targeting moiety.

Studies were conducted of the cytotoxicity of an immunotoxin made using a different antibody, SS1, which recognizes and binds mesothelin, an antigen present on the cells of many cancers. The SS1 antibody is described in, e.g., U.S. Pat. No. 7,081,518, and an immunotoxin comprising SS1 fused to PE38 (the immunotoxin is referred to as "SS1P") has been tested in a Phase I clinical trial. An immunotoxin was made using the SS1 antibody as the targeting moiety and the form of PE used in HA22-LR ("PE-LR") as the toxin moiety and the two immunotoxins, SS1P and SS1-PE-LR were tested for their cytotoxicity against a number of cell lines expressing mesothelin. The two immunotoxins had comparable activity against several cell lines. The SS1-PE-LR immunotoxin did have notably lower activity against some cell lines compared to SS1P. This indicates that, like most therapeutic agents, not all patients' cancers or other cells of interest will be susceptible to treatment with an immunotoxin using a PE-LR as the toxin moiety. Whether the growth of cells of any particular cancer or other target cells of interest can be inhibited can be readily determined by standard means, such as by taking a biopsy of the cells, contacting the cells with the PE-LR-containing immunotoxin, and determining if the immunotoxin inhibits growth of the cancer or other target cells to the desired extent.

Further, several means are known for increasing the cytotoxicity of PE by altering residues in domain III from the native sequence. Studies from the laboratory of the present inventors over a decade ago determined that certain amino acid sequences and repeats of these sequences could be used in place of the native sequence of residues 609-613 of PE to increase the cytotoxicity of the resulting PE compared to PE made with the native sequence (the native sequence of residues 609-613 and specific mutations that increase cytotoxicity are discussed in more detail below in the section entitled "*Pseudomonas* exotoxin A"). More recently, work from the laboratory of the present inventors indicated that a substitution of glycine, alanine, valine or other residues for the arginine present at position 490 of the native PE sequence would increase cytotoxicity, with substitution of the arginine by alanine being particularly advantageous. See, e.g., U.S. Published Patent Application 2007/0189962; Bang et al., Clin Cancer Res, 11:1545-1550 (2005). While PEs of the invention using the native domain III sequence are expected to be useful by themselves, if desired the cytotoxicity of the PE can be augmented by using one or more of these substitutions or mutations. Any particular substitution or mutation can be tested to determine whether it retains adequate cytotoxicity for in vitro use and whether it has sufficiently low non-specific toxicity for in vivo use using assays known in the art, including those set forth in the Examples.

Further, previous work from the laboratory of the present inventors has mapped the presence of epitopes or subepitopes in domain III. Binding of antibodies which recognize those epitopes can be reduced or eliminated by substitutions of the residues normally present at certain positions. As set forth in the U.S. Published patent application, the binding of these antibodies can be reduced by substituting an alanine, glycine, serine or glutamine for an amino acid residue corresponding to an amino acid residue of SEQ ID NO:1 selected from the group consisting of D403, R412, R427, E431, R432, R458, D461, R467, R505, R513, E522, R538, E548, R551, R576, K590, and L597. Since the presence of these residues prior to their substitution maintains an epitope or subepitope in domain III, for ease of reference, the residues at these positions can be referred to as "maintaining" the immunogenicity of their respective epitopes or subepitopes, while substituting them with alanine or the like reduces the immunogenicity of PE domain III resulting from the native epitope or subepitope. While PEs of the invention using the native domain III sequence are expected to be useful by themselves, therefore, if desired substitutions of one of more of the residues identified above can be made to reduce further the immunogenicity of the PEs of the invention. Any particular substitution or mutation can be tested to determine whether it retains adequate cytotoxicity for in vitro or in vivo use using assays known in the art, including those set forth in the Examples.

In preferred forms, the targeting agent of the chimeric molecules, such as immunotoxins, in which the PEs of the invention are used is not transforming growth factor α ("TGFα").

Furin and Furin Cleavable Sequences

As reported by Duckert et al., Protein Engineering, Design & Selection 17(1):107-112 (2004) (hereafter, "Duckert et al."), furin is an enzyme in a "family of evolutionarily conserved dibasic- and monobasic-specific CA2+-dependent serine proteases called substilisin/kexin-like proprotein convertases." Id., at p. 107. Furin, also known as "paired basic amino acid cleaving enzyme" or "PACE", is one of seven mammalian members of the family and is involved in processing several endogenous human proteins. See generally, e.g., Thomas G, *Nat Rev Mol Cell Biol*, (10):753-66 (2002). It is a membrane-associated protein found mainly in the trans-Golgi network. The sequence of human furin has been known since the early 1990s. See, e.g., Hatsuzawa, K. et al., *J. Biol Chem.*, 267:16094-16099 (1992); Molloy, S. et al., *J. Biol. Chem.*, 267:16396-16402 (1992).

The minimal cleavage site for furin is, in the single letter code for amino acid residues, R-X-X-R (SEQ ID NO:6), with cleavage occurring after the second "R". Duckert et al. summarizes the information available on the sequences of 38 proteins reported in the literature to have furin cleavage sites, including mammalian proteins, proteins of pathogenic bacteria, and viral proteins. It reports that 31, or 81%, of the cleavage motifs reviewed had the R-X-[R/K]-R (SEQ ID NO:7) consensus sequence, of which 11, or 29%, had R-X-R-R (SEQ ID NO:8), and 20, or 52%, were R-X-K-R (SEQ ID NO:9). Three of the cleavage motifs contained only the minimal cleavage sequence. Duckert et al. further aligned the motifs and identified the residues found at each position in each furin both for the cleavage motif itself and in the surrounding residues. FIG. 1A of Duckert et al. shows by relative size the residues most commonly found at each position. By convention, the residues surrounding the furin cleavage site are numbered from the scissile bond (which is typically indicated by the symbol "↓"). Counting toward the N terminus, the substrate residues are designated P1, P2, and so on, while counting towards the C-terminus, the residues are designated P1', P2', and so on. See, e.g., Rockwell, N. C., and J. W. Thorner, *Trends Biochem. Sci.*, 29:80-87 (2004); Thomas G., *Nat. Rev. Mol. Cell Biol.*, 3:753-766 (2002). Thus, following the convention, the following sequence can be used to align and number the residues of the minimal cleavage sequence and the surrounding residues:

P6-P5-P4-P3-P2-P1-P1'-P2'-P3'-P4'-P5', in which the minimal furin cleavage sequence is numbered as P4-P1. Duckert et al.'s alignment of 38 sequences cleaved by furin identifies the variations permitted depending on the residues present at various positions. For example, if the residue at P4 is not an R, that can be compensated for by having arginine or lysine residues at P2 and P6. Id., at p. 109.

In native PE, furin cleavage occurs between arginine 279 and glycine 280 in an arginine-rich loop located in domain II of the toxin. The native furin cleavage sequence in domain II of PE is set forth below (with numbers indicating the positions of the residues in the 613-amino acid native PE sequence), and aligned to show its numbering under the convention noted above:

```
274- R H R Q P R G W E Q L -284    (SEQ ID NO: 10)
P6-P5-P4-P3-P2-P1-P1'-P2'-P3'-
P4'-P5'
```

P6-P5-P4-P3-P2-P1-P1'-P2'-P3'-P4'-P5'
In studies underlying the present invention, substitutions were made at positions P3 and P2 to form the following sequence, with the substitutions underlined:

```
274- R H R S̲ K̲ R G W E Q L -284.    (SEQ ID NO: 11)
```

This sequence showed a cleavage rate faster than that of the native sequence, and when used in an exemplar immunotoxin (referred to as "JW008" for convenience of reference) resulted in cytotoxicity to target cells approximately the same as that of the native sequence.

Based on this and our previous studies, the furin cleavage sequence used to attach the targeting molecule to PE domain III can be the minimal furin cleavage sequence, R-X-X-R (SEQ ID NO:6), or any of the other furin cleavage sequences known in the art or permitted by FIG. 1A of Duckert et al., with the proviso that, if there is a residue present at the position identified as P2', it should be tryptophan or, if not tryptophan, should not be valine or alanine. For example, in some embodiments, the sequence can be RKKR (SEQ ID NO:12), RRRR (SEQ ID NO:13), RKAR (SEQ ID NO:14), SRVARS (SEQ ID NO:15), TSSRKRRFW (SEQ ID NO:16), or ASRRKARSW (SEQ ID NO:17).

As noted in Duckert et al., a less favorable residue than R (primarily valine) can be used position P4 if compensated for by arginine or lysine residues at positions P2 and P6, so that at least two of the three residues at P2, P4 and P6 are basic. Thus, in some embodiments, the furin cleavage sequence is RRVKKRFW (SEQ ID NO:18), RNVVRRDW (SEQ ID NO:19), or TRAVRRRSW (SEQ ID NO:20). The residue at position P1 can be the arginine present in the native sequence, or lysine. Thus, a lysine can be substituted for the arginine at position P1 in, for example, any the sequences set forth above.

In some embodiments, the sequence of the furin cleavable sequence follows the sequence of the furin cleavage sequence of PE: R-H-R-Q-P-R-G-W-E-Q-L (SEQ ID NO:10) or a truncated version of the native sequence, so long as it contains the minimal furin cleavage sequence and is cleavable by furin. Thus, in some embodiments, the furin cleavable sequence can be R-Q-P-R (SEQ ID NO:21), R-H-R-Q-P-R-G-W (SEQ ID NO:22), R-H-R-Q-P-R-G-W-E (SEQ ID NO:23), H-R-Q-P-R-G-W-E-Q (SEQ ID NO:24), or R-Q-P-R-G-W-E (SEQ ID NO:25). In some embodiments, the sequence is R-H-R-S-K-R-G-W-E-Q-L (SEQ ID NO:11), or a truncated version of this sequence, so long as it contains the minimal furin cleavage sequence and is cleavable by furin. Thus, in some embodiments, the furin cleavable sequence can be R-S-K-R (SEQ ID NO:26), R-H-R-S-K-R-G-W (SEQ ID NO:27), H-R-S-K-R-G-W-E (SEQ ID NO:28), R-S-K-R-G-W-E-Q-L (SEQ ID NO:29), H-R-S-K-R-G-W-E-Q-L (SEQ ID NO:30), or R-H-R-S-K-R (SEQ ID NO:31). Any particular furin cleavable sequence can be readily tested by making it into an immunotoxin with the antibody used in HA22 and testing the resulting immunotoxin in vitro on a CD22+ cell line. In preferred embodiments, the furin cleavable sequences do not reduce the cytotoxicity of the resulting immunotoxin below 10% of the cytotoxicity of that of HA22 when HA22 is tested on the same cell line, and more preferably do not reduce the cytotoxicity of the resulting immunotoxin below 15%, 20%, 25%, 30% 40%, 50%, 60%, 70%, 75%, 80%, 90% or higher of the cytotoxicity of HA22 when HA22 is tested on the same cell line, with each increasing percentage of cytotoxicity being more preferred than the one preceding it.

Whether or not any particular sequence is cleavable by furin can be determined by methods known in the art. For example, whether or not a sequence is cleavable by furin can be tested by incubating the sequence with furin in furin buffer (0.2 M NaOAc (pH 5.5), 5 mM $CaCl_2$) at a 1:10 enzyme:substrate molar ratio at 25° C. for 16 hours. These conditions have previously been established as optimal for furin cleavage of PE. Preferably, the furin used is human furin. Recombinant truncated human furin is commercially available, for example, from New England Biolabs (Beverly, Mass.). See also, Bravo et al., *J Biol Chem*, 269(14):25830-25837 (1994).

For clarity, it is noted that PEs currently in use, such as PE38 and PE40, comprise the native furin cleavage sequence, and that furin cleavage sequence is connected to PE domain III. Unlike the PEs of the invention, however, the furin cleavage sequence of PE38 and PE40 is not connected directly to domain III of these PEs; rather, they are connected to domain III through (a) 79 residues of domain II on the carboxyl side of the furin cleavage site (residues 285 to 364 of domain II; for convenience, these residues will be referred to as the "carboxyl residues of domain II"), plus (b) either residues 365-394 of SEQ ID NO:1, in the case of PE40, or residues 381-394 of SEQ ID NO:1, in the case of PE38. As discussed further herein, while the structural boundary of domain III of PE is considered to start at residue 405, functional analyses have shown that domain III requires a segment of domain Ib to retain ADP-ribosylating activity. Accordingly, the functional domain III is defined as residues 395-613 of PE, and it is thus preferred that the toxins of the invention comprise residues 395-613 of PE, with certain permitted variations described further below. For ease of reference, references herein to deletions of domain Ib or to the optional inclusion of some contiguous residues of domain Ib refer to the portion of domain Ib consisting of residues 365-394, even though structurally, domain Ib is understood to comprise residues 365-399.

Deletion of residues 365-394 and of the residues constituting domain II, other than those in the furin cleavage sequence, is desirable, as the deletions eliminate any immunogenic epitopes present in these portions of the PE molecule. In some embodiments, however, the practitioner may wish to retain some or all of residues 381-394, normally found in PE38, or to retain 1-10 residues on the amino or the carboxyl ends, or both, of the furin cleavage sequence, with 10, 9, 8, 7, 6, 5, 4, 3, 2 and 1 residues between successively more preferred. Typically, the residues on either side of the furin cleavage sequence are the residues normally present in the corresponding position of PE (SEQ ID NO:1). For example, as noted above, the furin cleavage sequence of PE is considered to end at residue 284. If the practitioner desires to extend the sequence to the carboxyl side by three residues, normally the residues chosen would be those present at positions 285-287 of SEQ ID NO:1. Thus, while in preferred embodiments, the term "furin cleavage sequence" refers to a 4 to 11 amino acid residue sequence cleavable by furin (as in the native furin cleavage sequence of PE, set forth above as SEQ ID NO:10), in some embodiments, it references such a sequence, further comprising 1-10 amino acid residues positioned at the amino or the carboxyl ends, or both.

As noted above, in PEs currently in use as toxic moieties, such as PE38 and PE40, the furin cleavage sequence is attached to domain III through the carboxyl sequence (residues 285-364) of domain II and through either residues 365-394 (in PE40) or through residues 381-394 (in PE38). In contrast, in the PEs of the invention, a furin cleavage sequence (such as SEQ ID NO:10, or truncated or modified variants thereof) is attached at its carboxyl end to domain III, without having interposed between the two some or all of the carboxyl residues of domain II, and preferably without having between the two some or all of residues 365-394.

The PEs of the invention can be represented by the formula:

$$R^1_n\text{-FCS-}R^2_n\text{-}R^3_n\text{-PE functional domain III}$$

wherein:

n=0 or 1 independently for each of $R^1$, $R^2$ and $R^3$,
$R^1$=1 to 10 amino acid residues;

FCS=a furin cleavage sequence of amino acid residues, which sequence is cleavable by furin and has an amino end and a carboxyl end;
$R^2$=1 to 10 amino acid residues;

$R^3$=one or more contiguous residues 365-394 of SEQ ID NO:1; and,

PE functional domain III=residues 395-613 of SEQ ID NO:1, optionally comprising (i) substitutions in one or more residues corresponding to 609-613 of SEQ ID NO:1, (ii) a substitution of glycine, alanine, valine, leucine, or isoleucine for arginine at a position corresponding to position 490 of SEQ ID NO:1, (iii) a substitution of one or more residues corresponding to residues of SEQ ID NO:1, which residues of SEQ ID NO:1 maintain immunogenicity of a epitope or subepitope of PE domain III, or (iv) a combination of any of (i)-(iii). In some embodiments, at least one of $R^1$, $R^2$ and $R^3$, n does not equal 0. As noted, in some preferred embodiments, all of residues 365-394 is deleted; thus, in these embodiments, in the term $R^3_n$, n=0. Similarly, in some embodiments, there are no residues on the amino side of the FCS; in these embodiments, in the term $R^1_n$, n=0, Similarly, in some embodiments, there are no residues on the carboxyl side of the FCS between the FCS and PE domains Ib or III; in these embodiments, in the term $R^2_n$, n=0. In particularly preferred embodiments, the n in $R^1_n$, $R^2_n$, and $R^3_n$, equals zero.

DEFINITIONS

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

*Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence (SEQ ID NO:1) is well known in the art and is set forth, for example, in SEQ ID NO:1 of U.S. Pat. No. 5,602,095. The method of action and structure of PE, as well as the modifications resulting in a number of variants of PE, are discussed in some detail in a section devoted to this purpose within Mutations of PE are typically described in the art by reference to the amino acid residue present at a particular position in the 613-amino acid sequence of native PE (SEQ ID NO:1). This convention is followed in this disclosure. If the amino acid residue present at a particular position has been replaced by another residue, as opposed, for example, to simply being deleted as part of a truncation of the native sequence, it is indicated by setting forth the residue present in the native sequence of PE, and the position number, followed by the amino acid residue with which the native residue has been replaced in the particular mutation under discussion. Thus, for example, the term "R490A" would indicate that the "R" (arginine, in standard single letter code) at position 490 of the native PE sequence (SEQ ID NO:1) has been replaced by an "A" (alanine, in standard single letter code) in the mutated PE under discussion. Similarly, "K590Q" would indicates that the lysine normally present at position 590 of PE has been replaced with a glutamine. The standard single letter code for common amino acids is set forth below.

The term "PE functional domain III" refers to residues 395-613 of native PE (the native sequence is SEQ ID NO:1). Although the structural boundaries of domain III have been set at residues 405-613, functional analyses have shown that domain III requires a segment of domain Ib to retain ADP-ribosylation activity (Hwang, J. et al., *Cell,* 48:129-136 (1987); Siegall, C. B. et al., *J Biol Chem,* 264:14256-14261 (1989)). The PE functional domain III is thus defined by residues 395-613 of PE (Kihara, A. and Pastan, I., *Bioconjug Chem,* 5:532-538 (1994)).

A variety of agents, such as cytokines, are known to bind to specific receptors on cell surfaces and can be used to targeted toxins to cells bearing such receptors. For example, IL-13 has been used as an agent to target toxins including forms of PE to cells over-expressing the IL-13 receptor. Antibodies bind specific antigens and are another type of agent used to direct toxins to desired target cells.

The term "ligand" is used herein to refer generically to molecules which bind specifically to a receptor or antigen on a cell surface. In preferred forms, the term encompasses both cytokines and antibodies or fragments thereof which retain recognition and binding capability for the antigen. In the most preferred form, the term refers to antibodies or fragments thereof which retain antigen recognition and binding capability.

The term "targeted toxin" refers to a toxin which is targeted to desired cells by a ligand which binds to specific receptors or antigens present on the surface of such cells. The term immunotoxins refers to a subset of targeted toxins in which the toxin is targeted to the desired cells by an antibody or fragment thereof.

Transforming growth factor α, or "TGFα" is a well known growth factor which in its mature form is a 5.5 kD, 50 amino acid protein. See, e.g., Brown, "The epidermal growth factor/transforming growth factor-α family and their receptors". Eur J Gastroenterol Hepatol 7:914-922 (1995); Soler C., and Carpenter G., Thomson A. W., ed. "The epidermal growth factor (EGF) family". The Cytokine Handbook, 3rd ed., San Diego, Calif., (pages 194-197 (1998). Recombinant human TGF α is commercially available from, for example, Sigma-Aldrich (catalog no. T7924, Sigma-Aldrich Corp., St. Louis, Mo.).

For convenience of reference, as used herein, the term "antibody" includes whole (which may also be referred to as "intact") antibodies, antibody fragments that retain antigen recognition and binding capability, whether produced by the modification of whole antibodies or synthesized de novo using recombinant DNA methodologies, monoclonal antibodies, polyclonal antibodies, and antibody mimics, unless otherwise required by context. The antibody may be an IgM, IgG (e.g. $IgG_1$, $IgG_2$, $IgG_3$ or $IgG_4$), IgD, IgA or IgE.

The term "antibody fragments" means molecules that comprise a portion of an intact antibody, generally the antigen binding or variable region of the intact antibody. Examples of antibody fragments include Fab, Fab', $F(ab')_2$, and Fv fragments; helix-stabilized antibodies (see, e.g., Arndt et al., *J Mol Biol,* 312:221-228 (2001); diabodies (see below); single-chain antibody molecules ("scFvs," see, e.g., U.S. Pat. No. 5,888,773); disulfide stabilized antibodies ("dsFvs", see, e.g., U.S. Pat. Nos. 5,747,654 and 6,558,672), and domain antibodies ("dAbs," see, e.g., Holt et al., *Trends Biotech,* 21(11): 484-490 (2003), Ghahroudi et al., *FEBS Lett.,* 414:521-526 (1997), Lauwereys et al., *EMBO* 17:3512-3520 (1998), Reiter et al., *J. Mol. Biol.,* 290:685-698 (1999), and Davies and Riechmann, *Biotechnology,* 13:475-479 (2001)).

The term "diabodies" refers to small antibody fragments with two antigen-binding sites, which fragments comprise a variable heavy domain ("$V_H$" or "VH") connected to a variable light domain ("$V_L$" or "VL") in the same polypeptide chain ($V_H$-$V_L$). By using a linker that is too short to allow pairing between the two domains on the same chain, the domains are forced to pair with the complementary domains of another chain and create two antigen-binding sites. Diabodies and their production are described more fully in, for example, EP 404,097; WO 93/11161; and Hollinger et al., *Proc. Natl. Acad. Sci. USA*, 90:6444-6448 (1993).

References to "$V_H$" or a "VH" refer to the variable region of an immunoglobulin heavy chain, including an Fv, scFv, dsFv or Fab. References to "$V_L$" or a "VL" refer to the variable region of an immunoglobulin light chain, including of an Fv, scFv, dsFv or Fab The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable domain of the heavy chain to the variable domain of the light chain.

The term "parental antibody" means any antibody of interest which is to be mutated or varied to obtain antibodies or fragments thereof which bind to the same epitope as the parental antibody, but with higher affinity.

The term "hotspot" means a portion of a nucleotide sequence of a CDR or of a framework region of a variable domain which is a site of particularly high natural variation. Although CDRs are themselves considered to be regions of hypervariability, it has been learned that mutations are not evenly distributed throughout the CDRs. Particular sites, or hotspots, have been identified as these locations which undergo concentrated mutations. The hotspots are characterized by a number of structural features and sequences. These "hotspot motifs" can be used to identify hotspots. Two consensus sequences motifs which are especially well characterized are the tetranucleotide sequence RGYW (SEQ ID NO:33) and the serine sequence AGY (SEQ ID NO:34), where R is A or G, Y is C or T, and W is A or T.

A "targeting moiety" is the portion of an immunoconjugate intended to target the immunoconjugate to a cell of interest. Typically, the targeting moiety is an antibody, or a fragment of an antibody that retains antigen recognition capability, such as a scFv, a dsFv, an Fab, or an F(ab')$_2$.

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond.

The phrase "disulfide stabilized Fv" or "dsFv" refer to the variable region of an immunoglobulin in which there is a disulfide bond between the light chain and the heavy chain. In the context of this invention, the cysteines which form the disulfide bond are within the framework regions of the antibody chains and serve to stabilize the conformation of the antibody. Typically, the antibody is engineered to introduce cysteines in the framework region at positions where the substitution will not interfere with antigen binding.

An antibody immunologically reactive with a particular antigen can be generated by recombinant methods such as selection of libraries of recombinant antibodies in phage or similar vectors, see, e.g., Huse et al., *Science*, 246:1275-1281 (1989); Ward, et al., *Nature*, 341:544-546 (1989); and Vaughan, et al., *Nature Biotech.*, 14:309-314 (1996), or by immunizing an animal with the antigen or with DNA encoding the antigen.

A "toxic moiety" is the portion of a immunotoxin which renders the immunotoxin cytotoxic to cells of interest.

A "therapeutic moiety" is the portion of an immunoconjugate intended to act as a therapeutic agent.

The term "therapeutic agent" includes any number of compounds currently known or later developed to act as antineoplastics, anti-inflammatories, cytokines, anti-infectives, enzyme activators or inhibitors, allosteric modifiers, antibiotics or other agents administered to induce a desired therapeutic effect in a patient. The therapeutic agent may also be a toxin or a radioisotope, where the therapeutic effect intended is, for example, the killing of a cancer cell.

A "detectable label" means, with respect to an immunoconjugate, a portion of the immunoconjugate which has a property rendering its presence detectable. For example, the immunoconjugate may be labeled with a radioactive isotope which permits cells in which the immunoconjugate is present to be detected in immunohistochemical assays.

The term "effector moiety" means the portion of an immunoconjugate intended to have an effect on a cell targeted by the targeting moiety or to identify the presence of the immunoconjugate. Thus, the effector moiety can be, for example, a therapeutic moiety, a toxin, a radiolabel, or a fluorescent label.

The term "immunoconjugate" includes reference to a covalent linkage of an effector molecule to an antibody. The effector molecule can be a toxin.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "toxin" includes reference to abrin, ricin, *Pseudomonas* exotoxin A (PE), diphtheria toxin (DT), botulinum toxin, or modified toxins thereof. For example, PE and DT are highly toxic compounds that typically bring about death through liver toxicity. PE and DT, however, are typically modified for use as an immunotoxin by removing the native targeting component of the toxin (e.g., domain Ia of PE or the B chain of DT) and replacing it with a different targeting moiety, such as an antibody.

The term "contacting" includes reference to placement in direct physical association.

An "expression plasmid" comprises a nucleotide sequence encoding a molecule or interest, which is operably linked to a promoter.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

Amino Acid Nomenclature

| Name | 3-letter | 1-letter |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B each contain amino acids that are conservative substitutions for one another:

TABLE B

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *Proteins: Structures and Molecular Properties*, W. H. Freeman and Company, New York (2nd Ed., 1992).

The terms "substantially similar" in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "attaching," "conjugating," "joining," "bonding" or "linking" refer to making two polypeptides into one contiguous polypeptide molecule. In the context of the present invention, the terms include reference to joining an antibody moiety to a PE of the invention. The linkage can be either by chemical or recombinant means. Chemical means refers to a reaction between the antibody moiety and the PE molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (*Proc. Nat'l Acad. Sci. USA,* 82:2306-2309 (1985)), or the ciliate *Macronucleus,* may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli,* or eukaryotic cells such as yeast, insect, amphibian, or mammalian cells.

The phrase "phage display library" refers to a population of bacteriophage, each of which contains a foreign cDNA recombinantly fused in frame to a surface protein. The phage display the foreign protein encoded by the cDNA on its surface. After replication in a bacterial host, typically *E. coli,* the phage which contain the foreign cDNA of interest are selected by the expression of the foreign protein on the phage surface.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, more preferably 65%, even more preferably 70%, still more preferably 75%, even more preferably 80%, and most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.,* 2:482 (1981), by the homology alignment algorithm of Needleman & Wunsch, *J Mol. Biol.,* 48:443 (1970), by the search for similarity method of Pearson & Lipman, *Proc. Nat'l. Acad. Sci. USA,* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology,* F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al., *J. Mol. Biol.,* 215:403-410 (1990) and Altschuel et al. *Nucleic Acids Res.,* 25:3389-3402 (1977), respectively. Software for performing BLAST analyses is publicly available through the National Center for Biotechnology Information (available on the internet by entering "http://www.ncbi." followed by "nlm.nih.gov/"). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci. USA,* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA,* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, preferably greater than 5-fold, more preferably greater than 10-fold and most preferably greater than 100-fold increase in amount of bound antibody (per unit time) to a cell or tissue bearing a target antigen as compared to a cell or tissue lacking the target antigen. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Pseudomonas Exotoxin A

Native Pseudomonas exotoxin A ("PE") is an extremely active monomeric protein (molecular weight 66 kD), secreted by Pseudomonas aeruginosa, which inhibits protein synthesis in eukaryotic cells. The native PE sequence (SEQ ID NO:1) is well known and is set forth, for example, in SEQ ID NO:1 of U.S. Pat. No. 5,602,095. The method of action is inactivation of the ADP-ribosylation of elongation factor 2 (EF-2).

PE has been studied for over 20 years for use as a therapeutic agent. The exotoxin contains three structural domains that act in concert to cause cytotoxicity. Domain Ia (amino acids 1-252) mediates cell binding Domain II (amino acids 253-364) is responsible for translocation into the cytosol and domain III (amino acids 400-613) mediates ADP ribosylation of elongation factor 2. The function of domain Ib (amino acids 365-399) remains undefined, although it has been known a large part of it, amino acids 365-380, can be deleted without loss of cytotoxicity. See Siegall et al., *J Biol Chem*, 264:14256-14261 (1989).

The terms "*Pseudomonas* exotoxin" and "PE" as used herein typically refer to a PE that has been modified from the native protein to reduce binding and uptake via LRP1/CD91 (the cell surface receptor bound by the full-length toxin), to eliminate folding problems, or to reduce non-specific toxicity. Numerous such modifications are known in the art and include, but are not limited to, elimination of domain Ia, various amino acid deletions in domains Ib, II and III, single amino acid substitutions and the addition of one or more sequences at the carboxyl terminus such as KDEL (SEQ ID NO:2) and REDL (SEQ ID NO:3). See Siegall et al., supra. Cytotoxic fragments of PE include those which are cytotoxic with or without subsequent proteolytic or other processing in the target cell (e.g., as a protein or pre-protein).

Certain cytotoxic fragments of PE are known in the art and are often referenced by the molecular weight of the fragment, which designates for the person of skill in the art the particular composition of the PE fragment. For example, PE40 was one of the first fragments that was studied and used as the toxic portion of immunotoxins. The term designates a truncated form of PE in which domain I, the domain responsible for non-specific binding. See, e.g., Pai et al., *Proc. Nat'l Acad. Sci. USA*, 88:3358-3362 (1991); and Kondo et al., *J. Biol. Chem.*, 263:9470-9475 (1988). Elimination of non-specific binding, however, can also be achieved by mutating certain residues of domain Ia. U.S. Pat. No. 5,512,658, for instance, discloses that a mutated PE in which domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as "PE4E."

The term "PE38" refers to a cytotoxic fragment of PE composed of amino acids 253-364 and 381-613 of PE and having a molecular weight of approximately 38 kD. It contains the translocating and ADP ribosylating domains of PE, but not the cell-binding portion (Hwang J. et al., *Cell*, 48:129-136 (1987)). PE38 is a pro-protein which is activated to its cytotoxic form upon processing within a cell (see, e.g., U.S. Pat. No. 5,608,039, and Pastan et al., *Biochim. Biophys. Acta*, 1333:C1-C6 (1997)). The sequence of PE38 is well known in the art, but can also readily be determined by the practitioner by subtracting the stated residues from the known sequence of PE. Persons of skill will be aware that, due to the degeneracy of the genetic code, the amino acid sequence of PE38, of its variants, such as PE38 KDEL or PE38QQR, and of the other PE derivatives discussed herein can be encoded by a great variety of nucleic acid sequences, any of which can be expressed to result in the desired polypeptide.

"PE35" is a 35 kD carboxyl-terminal fragment of PE in which amino acid residues 1-279 have deleted and the molecule commences with a methionine at position 280, followed by amino acids 281-364 and 381-613 of native PE. PE35 and PE40 are disclosed in U.S. Pat. Nos. 5,602,095 and 4,892,827.

Studies also determined that mutations of the terminal residues of PE, REDLK (SEQ ID NO:5, residues 609-613) could be varied in ways that would increase the cytotoxicity of the resulting mutant. For example, immunotoxins made with mutated PEs ending in the sequences KDEL (SEQ ID NO:2), REEL (SEQ ID NO:32) or RDEL (SEQ ID NO:3) were much more cytotoxic to target cells than were like immunotoxins made with PE38 bearing the native terminal sequence. See, Kreitman and Pastan, *Biochem J*, 307(Pt 1):29-37 (1995). Repeats of these sequences can also be used. See, e.g., U.S. Pat. Nos. 5,854,044; 5,821,238; and 5,602,095 and International Publication WO 99/51643. While PEs terminating in KDEL (SEQ ID NO:2) are useful for in vitro purposes, they proved to have non-specific toxicity in animals and are less preferred for in vivo use.

In a preferred embodiment, the cytotoxic fragment of PE retains at least about 10%, preferably at least about 40%, more preferably about 50%, even more preferably 75%, more preferably at least about 90%, and still more preferably 95% of the cytotoxicity of PE38. In particularly preferred embodiments, the cytotoxic fragment has at least the cytotoxicity of PE38, and preferably has more.

A. Conservatively Modified Variants of PE

It is understood that the sequence of native PE and the variants discussed above can have conservative substitutions and retain cytotoxic capability and, desirably, reduced antigenicity compared to the native sequence of PE. In preferred embodiments, modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG and TGG, which are ordinarily the only codons for methionine and tryptophan, respectively) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

B. Assaying for Cytotoxicity or Antigenicity of PE

*Pseudomonas* exotoxins employed in the invention can be assayed for the desired level of cytotoxicity by assays well known to those of skill in the art. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE. Antigenicity can be assayed by, for example, the methods taught in the Examples herein.

C. Conjugation to a Targeting Molecule

In non-recombinant embodiments of the invention, a targeting molecule, such as an antibody, is linked to a PE molecule of the present invention using any number of means known to those of skill in the art. Both covalent and noncovalent attachment means may be used with PE molecules of the present invention. The procedure for attaching a PE molecule to an antibody or other targeting molecule ("TM") will vary according to the chemical structure of the TM. Polypeptides typically contain a variety of functional groups; e.g., carboxylic acid (COOH), free amine (—NH$_2$) or sulfhydryl (—SH) groups, which are available for reaction with a suitable functional group on an antibody, for example, to result in the binding of the PE molecule.

Alternatively, the antibody or other TM is derivatized to expose or to attach additional reactive functional groups. The derivatization may involve attachment of any of a number of linker molecules, such as those available from Pierce Chemical Company, Rockford Ill.

Production of Immunoconjugates

Immunoconjugates of the invention include, but are not limited to, molecules in which there is a covalent linkage of a PE molecule to an antibody or other targeting agent. The choice of a particular targeting agent depends on the particular cell to be targeted. With the PE molecules provided herein, one of skill can readily construct a variety of clones containing functionally equivalent nucleic acids, such as nucleic acids which differ in sequence but which encode the same PE and antibody sequence. Thus, the present invention provides nucleic acids encoding antibodies and PE conjugates and fusion proteins thereof.

A. Recombinant Methods

The nucleic acid sequences of the present invention can be prepared by any suitable method including, for example, cloning of appropriate sequences or by direct chemical synthesis by methods such as the phosphotriester method of Narang et al., *Meth. Enzymol.*, 68:90-99 (1979); the phosphodiester method of Brown et al., *Meth. Enzymol.*, 68:109-151 (1979); the diethylphosphoramidite method of Beaucage et al., *Tetra. Lett.*, 22:1859-1862 (1981); the solid phase phosphoramidite triester method described by Beaucage & Caruthers, *Tetra. Letts.*, 22(20):1859-1862 (1981), e.g., using an automated synthesizer as described in, for example, Needham-VanDevanter et al., *Nucl. Acids Res.*, 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook et al., MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL, Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding native PE can also be modified to form the immunoconjugates of the present invention. Modification by site-directed mutagenesis is well known in the art. Nucleic acids encoding PE can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an antibody or other TM of choice into a vector which comprises the cDNA encoding a desired PE of the invention. The insertion is made so that the targeting agent (for ease of discussion, the discussion herein will assume the targeting agent is an Fv, although other targeting agents could be substituted with equal effect) and the PE are read in frame, that is in one continuous polypeptide which contains a functional Fv region and a functional PE region. In a particularly preferred embodiment, cDNA encoding a PE of the invention is ligated to a scFv so that the toxin is located at the carboxyl terminus of the scFv. In other preferred embodiments, cDNA encoding a PE of the invention is ligated to a scFv so that the toxin is located at the amino terminus of the scFv.

Once the nucleic acids encoding a PE, antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., PE or an immunoconjugate formed from a PE of the invention) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

In addition to recombinant methods, the immunoconjugates and PEs of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A, pp. 3-284; Merrifield et al., *J. Am. Chem. Soc.*, 85:2149-2156 (1963), and Stewart et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

B. Purification

Once expressed, the recombinant immunoconjugates and PEs of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies of this invention. See, Buchner et al., *Anal. Biochem.*, 205:263-270 (1992); Pluckthun, *Biotechnology*, 9:545 (1991); Huse et al., *Science*, 246:1275 (1989) and Ward et al., *Nature*, 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry*, 9: 5015-5021 (1970), incorporated by reference herein, and especially as described by Buchner et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione, and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5-fold molar excess of one protein over the other is not exceeded. It is desirable to add excess oxidized glutathione or other oxidizing low molecular weight compounds to the refolding solution after the redox-shuffling is completed.

Pharmaceutical Compositions and Administration

The immunoconjugate compositions of this invention (i.e., PE linked to an antibody on other targeting agent) are particularly useful for parenteral administration, such as intravenous administration or administration into a body cavity.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical immunotoxin composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339 (1992), both of which are incorporated herein by reference.

Polymers can be used for ion-controlled release of immunoconjugate compositions of the present invention. Various degradable and nondegradable polymeric matrices for use in controlled drug delivery are known in the art (Langer R., *Accounts Chem. Res.*, 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.*, 9:425-434 (1992); and Pec et al., *J. Parent. Sci. Tech.*, 44(2):58-65 (1990)). Alternatively, hydroxyapatite has been used as a microcarrier for controlled release of proteins (Ijntema et al., *Int. J. Pharm.*, 112:215-224 (1994)). In yet another aspect, liposomes are used for controlled release as well as drug targeting of the lipid-capsulated drug (Betageri et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins of the present invention are included a variety of disease conditions caused by specific human cells that may be eliminated by the toxic action of the fusion protein.

In Vitro Uses

In another embodiment, this invention provides for kits for eliminating target cells in vitro or ex vivo using PEs of the invention. For example, immunotoxins comprising a PE of the invention can be used to purge targeted cells from a population of cells in a culture. Thus, for example, cells cultured from a patient having a cancer expressing CD22 can be purged of cancer cells by contacting the culture with immunotoxins which use anti-CD22 antibodies as a targeting moiety.

In some instances, the target cells may be contained within a biological sample. A "biological sample" as used herein is a sample of biological tissue or fluid that contains target cells and non-target cells. Such samples include, but are not limited to, tissue from biopsy, blood, and blood cells (e.g., white cells). A biological sample is typically obtained from a multicellular eukaryote, preferably a mammal such as rat, mouse, cow, dog, guinea pig, or rabbit, and more preferably a primate, such as a macaque, chimpanzee, or human. Most preferably, the sample is from a human.

EXAMPLES

Example 1

This Example sets forth materials and methods used in some of the studies underlying the present invention.

Lysosomal Preparation of Raji Cells

Raji Burkitt's lymphoma cells ($1-3\times10^8$) were harvested, washed twice in cold PBS, once in homogenization buffer (250 mM sucrose, 1 mM EDTA) and resuspended in 2 ml of homogenization buffer. Cells in suspension were lysed by nitrogen cavitation with a 45 ml-cell disruption bomb (Parr Instrument Company, Moline, Ill.) chilled to 4° C. and pressurized with nitrogen gas to 150-200 psi for 10 min. The disrupted cells were spun at 800×g for 10 min. The post-nuclear supernatant (middle layer) was removed and layered atop an 8.5 ml 27% PERCOLL® solution cushioned on a 1.2 ml layer of 10× homogenization buffer in a 16×76 Ultraclear Beckman centrifuge tube (Beckman Coulter, Inc., Fullerton, Calif.) and spun at 4° C. in a Beckman Type 50 Ti rotor for 1 h at 36,000×g. Fractions from the PERCOLL® gradient were collected and then assayed individually for β-hexosaminidase activity as described (Schaub, B. E. et al., *Curr Protoc Cell Biol*, 15:8.1-8.12 (2005)). The fractions with peak activity were pooled, transferred to 13×51 mm thick-walled polycarbonate tubes, and spun at 4° C. using a S100AT4-542 rotor for 30 min at 200,000×g to remove the PERCOLL®. The supernatant was collected and used to digest immunotoxins.

Lysosomal Protease Digestion of B3(dsFv)-PE38 and N-Terminal Sequencing of the Fragments Purified lysosomal proteases cathepsin B, cathepsin D, and cathepsin S (EMD Biosciences, San Diego, Calif.), or the lysosomal fraction of Raji cells were used to digest the immunotoxin B3(dsFv)-PE38. B3(dsFv)-PE38 (0.2 mg/ml) was incubated either with 5 μg/ml of the purified cathepsin lysosomal proteases (cathepsins B, D, and S) or with 30% (v/v) of the lysosomal fraction of Raji cells at 37° C. in buffer containing 0.1 M MES (pH 5.5), 150 mM NaCl, 2 mM DTT, 2 mM EDTA, and 0.5% Triton X-100. At time intervals between 0 and 60 h following the start of incubation, aliquots were removed into tris-glycine SDS-PAGE sample buffer and incubated at 85° C. for 5 min. Half of each sample was run on a Novex 4-20% acrylamide tris-glycine protein gel (Invitrogen Corporation, Carlsbad, Calif.) and visualized using the Microwave Blue Coomassie blue protein stain (Protiga Inc., Frederick, Md.). The remaining sample was fractionated by gel electrophoresis in the same manner and then electroblotted onto PVDF membrane (ProBlott; Applied Biosystems, Inc., Foster City, Calif.) in a 10 mM CAPC buffer (pH 11) using a semidry transfer unit. After blotting the membrane was briefly rinsed with water, stained with 0.1% Coomasie Blue R-250 in 0.5% acetic acid/40% methanol for 2 min, and then distained in 50% methanol in water. Protein bands were excised from the membrane and analyzed using a Procise 494 cLC automated protein sequencer (Applied Biosystems, Inc.).

Mutations in HA22

Mutations in HA22 were generated using Quikchange site-directed mutagenesis (Stratagene, La Jolla, Calif.) with mutagenesis primers from Lofstrand Labs Limited (Gaithersburg, Md.).

Purification of immunotoxins—Immunotoxins were purified as described (Pastan, I. et al., *Methods Mol Biol*, 248: 503-518 (2004)), except that oxidized, not reduced, glutathione was added to the refolding buffer.

Cell Lines

CD22-positive human Burkitt lymphoma cell lines (CA46, Daudi, Raji, and Ramos) were obtained from American Type Culture Collection (Manassas, Va.). The KOPN-8 ALL cell line was obtained from Dr. Alan Wayne at the National Cancer Institute (Bethesda, Md.). The WSU-CLL cell line [which may actually be a derivative of the REH ALL cell line (Drexler, H. G. et al., *Leukemia*, 16:1868-1870 (2002))] was obtained from Dr. A. Al-Katib (Wayne State University, Detroit, Mich.). All cell lines were grown at 37° C. with 5% $CO_2$ in RPMI-1640 medium supplemented with 10% FBS, 2 mM L-glutamine, 1 mM sodium pyruvate, 100 U penicillin, and 100 μg streptomycin (Invitrogen Corporation, Carlsbad, Calif.).

Cytotoxicity Assays

Cell survival of cell lines treated with immunotoxins was measured by WST-8 assay using the Cell Counting Kit-8 (Dojindo Molecular Technologies, Inc., Gaithersburg, Md.) essentially as described in the technical manual. Briefly, 10,000 cells/well were incubated with toxin in a 96-well plate (Pastan, I. et al., *Methods Mol Biol*, 248:503-518 (2004)) for 48-72 h, after which the CCK-8 reagent was added to wells. Plates were incubated until the wells with the maximum absorbance at 450 nm reached values of ~1 OD. Cyclohexamide (10 μg/ml final concentration) was used as a control for 100% cell death. Values were normalized between the cyclohexamide and PBS/HSA (0.2%) controls and fit to a standard 4-parameter sigmoidal equation with a variable slope using the GraphPad PRISM® (v 2.00) (GraphPad Software, Inc., La Jolla, Calif.) program to obtain the concentration of immunotoxin at which there was 50% cell death ($IC_{50}$). Cells from patients with CLL and HCL were assayed as previously described (Kreitman, R. J. et al., *Clin. Cancer Res.*, 6:1476-1487 (2000)). Briefly, leukemia cells were incubated with recombinant immunotoxins for 3 days, then treated with $^3$H-leucine to assess protein synthesis inhibition or with WST-1 to assess cell death.

Statistical Analysis

The $IC_{50}$ values from matched pairs of cytotoxicity assays analyzing the effect of HA22 and HA22-LR on the survival of Raji (n=10), Ramos (n=3), Daudi (n=3), CA46 (n=5), KOPN8 (n=3), and WSU-CLL (n=4) cell lines were compared using a paired, two-tailed t-test.

Nonspecific Mouse Toxicity

Female nude mice (5-6 wk, 18-22 g) were intravenously injected with a single dose of 2.0 mg/kg HA22 or HA22-LR ranging from 2.5-20 mg/kg in 0.2 ml PBS containing 0.2% HSA. Mice were observed for 10 days. All procedures involving mice were conducted in accordance with National Institutes of Health guidelines as approved by the Animal Care and Use Committee of the National Cancer Institute.

Pharmacokinetics—

Nine female Balb/c mice were injected in the tail vein with 10 µg HA22 or HA22-LR in 0.2 ml of PBS with 0.2% HSA. Blood samples were taken from three separate mice at time intervals of 2, 5, 10, 20, 30, and 60 min from the time of injection, and each mouse was bled twice. Groups of three mice were bled at time intervals of 2 and 60 min, 5 and 30 min, or 10 and 20 min. Serum was harvested from the blood samples and analyzed by ELISA (Bang S. et al., Clin Cancer Res, 11:1545-1550 (2005)) in comparison to a standard curve of the corresponding pure immunotoxin in order to determine the concentration of immunotoxin in the mouse serum.

Mouse Xenograft Antitumor Activity—

Forty female severe combined immunodeficiency (SCID) mice were injected subcutaneously with $10^7$ CA46 cells on day 0 as described previously (Kreitman, R. J. et al., Int J Cancer, 81:148-155 (1999)). Tumor volume was measured regularly by caliper for the next 6 weeks. When the average size reached ~120 mm$^3$, 6 days following implantation, mice were divided into five groups of eight and injected QOD X 3 with 0.2 ml of PBS containing 0.2% HSA and either HA22 (0.3 mg/kg) or HA22-LR (1.0, 1.75, or 2.5 mg/kg), or left untreated (PBS/0.2% HSA alone). Mice were euthanized if their tumors exceeded 1000 mm$^3$ or at the end of the 10-wk experiment.

Example 2

This Example sets forth the results of PE lysosomal protease cleavage studies. Immunotoxins are internalized into cells via target-mediated endocytosis, and must reach the cytosol to exert their toxic effect. Since lysosomes are the major degradative pathway for exogenous, internalized macromolecules, immunotoxins must avoid lysosomal degradation on their path to the cytosol (Fitzgerald, D., Semin Cancer Biol, 7:87-95 (1996)). Therefore, studies were performed to determine if an immunotoxin could be produced by identifying and removing lysosomal protease cleavage sites in the immunotoxin.

Lysosomal Protease Digestion of Immunotoxins

To determine the location of the lysosomal protease cleavage sites within immunotoxins, a large quantity of a highly purified immunotoxin was required. A large stock of immunotoxin B3(dsFv)-PE38, which contains the same PE38 fragment as HA22 but with a different Fv as the targeting moiety, was available (Reiter, Y. et al., Cancer Res, 54:2714-2718 (1994)). B3(dsFv)-PE38 was incubated either with lysosomal extracts prepared from Raji cells or with purified lysosomal proteases cathepsin B, cathepsin D, or cathepsin S. Aliquots of the reaction were removed at times between 0 and 60 h, and fragments were separated and visualized by reducing SDS-PAGE.

Each gel showed two expected bands at time 0 that correspond to the disulfide-linked polypeptides VL-PE38 and VH, which migrate at approximately 50-kDa and 12-kDa, respectively. Digestion of B3(dsFv)-PE38 with lysosomal extract showed five cleavage fragments of 38-kDa (Lys-1), 30-kDa (Lys-2), 27-kDa (Lys-3), 25-kDa (Lys-4), and 23-kDa (Lys-5). Cathepsin B digestion showed three fragments of 38-kDa (B-1), 30-kDa (B-2), and 25-kDa (B-3). Cathepsin D digestion showed at least five fragments: 36-kDa (D-1), 30-kDa (D-2), 15-kDa (D-3), 14-kDa (D-4), and 13-kDa (D-5). Digestion with Cathepsin S showed four fragments: 38-kDa (S-1), 30-kDa (S-2), 25-kDa (S-3), and 13-kDa (S-4). The four digests contain several fragments that migrate with similar molecular weights, suggesting that the cleavage sites may be similar.

To locate the cleavage sites, the fragments were separated by SDS-PAGE, immobilized by electroblotting, and sequenced using Edman degradation. The N-terminal sequences were compared with the sequence of B3(dsFv)-PE38 to determine the locations of the cleavage sites. The sequences of several fragments correspond to the N-terminus of B3(dsFv)-PE38 VL-PE38 (Lys-4, Lys-5, D-5, and S-4). The remaining fragments are located in domains II or Ib of PE38. No cleavage sites were found in the Fv or PE domain III.

Removal of Protease-Susceptible Regions

Since there are numerous lysosomal proteases with broad and often overlapping specificity, and the observed sites cluster in a limited segment of PE38, cleavage sites were eliminated by making deletions to remove the sites.

Although B3(dsFv)-PE38 was used to study the cleavage sites, it is no longer being pursued for therapeutic use. Another PE38-based immunotoxin, HA22, was used to study the effects of the site deletions. HA22 is an affinity-optimized, more active variant of the anti-CD22 immunotoxin BL22 (Salvatore, G. et al., Clin Cancer Res, 8:995-1002 (2002)), and is currently in clinical trials for the treatment of B cell malignancies (chronic lymphocytic leukemia [CLL], hairy cell leukemia [HCL], and acute lymphoblastic leukemia [ALL]). A series of deletions removing large segments of domains II and Ib from PE38 were introduced into HA22. The mutant proteins were expressed, purified, and compared to HA22 in vitro using cytotoxicity assays on Raji cells.

FIG. 3 indicates the portion of the native PE sequence remaining in HA22 and in further mutated forms of PE (denoted as M1-M5) created in the course of the present studies, and the activities of M1-M5 relative to HA22 on Raji cells. Removal of residues 251 to 273 (M1) or 365 to 394 (M2) does not substantially affect immunotoxin activity. Likewise, deleting residues 251 to 273 and 350 to 394, along with changing a free cysteine at position 287 to serine (M3), yields a fully active immunotoxin. The C287S mutation combined with the deletion of residues 350 to 394 and 251 to 280 (M4), which eliminates furin cleavage at Arg279, yields an immunotoxin that is approximately 5-fold less active than HA22. Unexpectedly, a mutant with large deletions that removed most residues and all cleavage sites from domain II and Ib (M5) was still highly active. The M5 mutant retains only an 11-residue sequence (274-284) in domain II containing the furin recognition and Arg279 cleavage site.

The M5 HA22 mutant was redesignated as "HA22-LR" to indicate that it is "lysosome resistant." To verify that HA22-LR is resistant to lysosomal degradation, it was treated with lysosomal extracts and examined by SDS-PAGE over 24 h. While HA22 is largely hydrolyzed into smaller fragments by 30 min and completely fragmented after 4 h, proteolysis of HA22-LR was much slower, with barely detectable hydrolysis at 2 h and a considerable intact fraction still detectable after 24 h.

Example 3

This Example sets forth the results of studies of the activity of HA22-LR on CD22-positive cell lines.

The activity of HA22-LR was investigated on additional CD22-positive tumor cell lines and compared to HA22 using a paired, two-tailed t-test between the resulting $IC_{50}$ values (Table 1). HA22-LR had activity indistinguishable from HA22 on the Ramos (n=3), CA46 (n=5), and Daudi (n=3) lymphoma cell lines, but had significant differences against the WSU-CLL cell line (212% activity, p=0.01, n=4), the KOPN-8 ALL cell line (22% activity, p=0.01, n=3), and the Raji cell line (49%, p=0.0002, n=10). Although there is some variability in the activity of HA22-LR, HA22-LR and HA22 had generally similar activities on CD22-positive cell lines.

TABLE 1

Activity of HA22 and HA22-LR on six CD22-positive cell lines
$IC_{50} \pm SE$ (ng/ml)

| Cell Line | HA22 | HA22-LR | Relative Activity |
|---|---|---|---|
| CA46 (n = 5) | 0.30 ± 0.08 | 0.26 ± 0.06 | 1.15 |
| Daudi (n = 3) | 0.27 ± 0.04 | 0.24 ± 0.04 | 1.12 |
| Ramos (n = 3) | 1.62 ± 0.28 | 1.78 ± 0.15 | 0.91 |
| Raji* (n = 10) | 0.36 ± 0.04 | 0.73 ± 0.09 | 0.49 |
| KOPN-8* (n = 3) | 0.10 ± 0.02 | 0.45 ± 0.05 | 0.22 |
| WSU-CLL* (n = 4) | 2.50 ± 0.53 | 1.18 ± 0.34 | 2.12 |

*Indicates a significant difference (p < 0.05 in a paired, two-tailed t-test) between the $IC_{50}$ values of HA22 and HA22-LR.

Example 4

This Example sets forth the results of studies of the activity of HA22-LR on CD22-positive malignant cells freshly obtained from patients.

To determine if the new immunotoxin would also kill cells obtained directly from patients, it was tested on cells from 5 patients with CLL and 3 with HCL. As shown in Table 2, activity was observed for all patient cell populations tested with HA22-LR. In CLL, malignant cells from all 5 patients were more sensitive to HA22-LR than to HA22, by a median of over 17-fold (p=0.009, Wilcoxon). $IC_{50}$s for the inhibition of protein synthesis ranged from <1 to 5.6 ng/ml. HA22-LR inhibited protein synthesis by 55% at 1 ng/ml in cells from patient CLL #2 ($IC_{50}$<1 ng/ml). Assays for cell death in CLL patient cells also showed more sensitivity to HA22-LR than to HA22. While the $IC_{50}$s of HA22 in CLL patient cells varied widely from 8 to >1000 ng/ml, $IC_{50}$s of HA22-LR varied by less than 10-fold. In HCL, HA22-LR was generally less active than HA22 with respect to protein synthesis inhibition. Assays for cell death in two of the three HCL patient cell populations showed similar findings. In summary HA22-LR was highly cytotoxic toward CD22-positive CLL and HCL cells, but among CLL cells, which displayed variable sensitivity toward HA22, the cytotoxicity of HA22-LR was significantly more potent and more uniform.

TABLE 2

Cytotoxicity of HA22 and HA22-LR toward Chronic Lymphocytic Leukemia (CLL) and Hairy Cell Leukemia (HCL) cells freshly obtained from patients
$IC_{50} \pm SD$ (ng/ml)

| Type and Patient No. | HA22 | HA22-LR | Relative Activity | Assay type |
|---|---|---|---|---|
| CLL #1 | >1000 | 4.7 ± 0.54 | >210 | Protein synthesis |
| CLL #1 | 55 ± 12.8 | 3.4 ± 0.53 | 16.2 | Cell death |
| CLL #2 | 16.8 ± 1.05 | <1 | >16.8 | Protein synthesis |
| CLL #2 | 10.1 ± 0.48 | 1.32 ± 0.164 | 7.65 | Cell death |
| CLL #3 | 8.1 ± 2.1 | 3.9 ± 0.50 | 2.07 | Protein synthesis |
| CLL #4 | 290 ± 167 | 5.6 ± 1.10 | 51.8 | Protein synthesis |
| CLL #5 | 8.0 ± 1.51 | 3.7 ± 0.27 | 2.16 | Protein synthesis |
| HCL #1 | 5.2 ± 0.37 | 5.9 ± 1.03 | 0.88 | Protein synthesis |
| HCL #2 | 0.177 ± 0.0062 | 1.25 ± 0.24 | 0.14 | Protein synthesis |
| HCL #2 | 0.165 ± 0.0098 | 2.0 ± 0.39 | 0.08 | Cell death |
| HCL #3 | 1.76 ± 0.51 | <1 | >1.76 | Protein synthesis |
| HCL #3 | 2.1 ± 0.51 | 1.51 ± 0.29 | 1.39 | Cell death |

Example 5

This Example sets forth the results of studies of toxicity and pharmacokinetics of HA22-LR in mice.

Toxicity Studies

Nude mice were injected intravenously with a single dose of HA22-LR ranging from 2.5 to 20 mg/kg and observed for 10 days. No deaths were observed through the mg/kg dose level (Table 3). Higher doses were not evaluated. In marked contrast, and consistent with previous data (Bang, S. et al., *Clin Cancer Res*, 11:1545-1550 (2005)), a 2.0 mg/kg dose of HA22 produced death in 100% (5/5) of mice. The single-dose i.v. $LD_{50}$ of HA22-LR is greater than 20 mg/kg, indicating a decrease in nonspecific toxicity of more than 10-fold relative to HA22.

Pharmacokinetics

Figure 5:
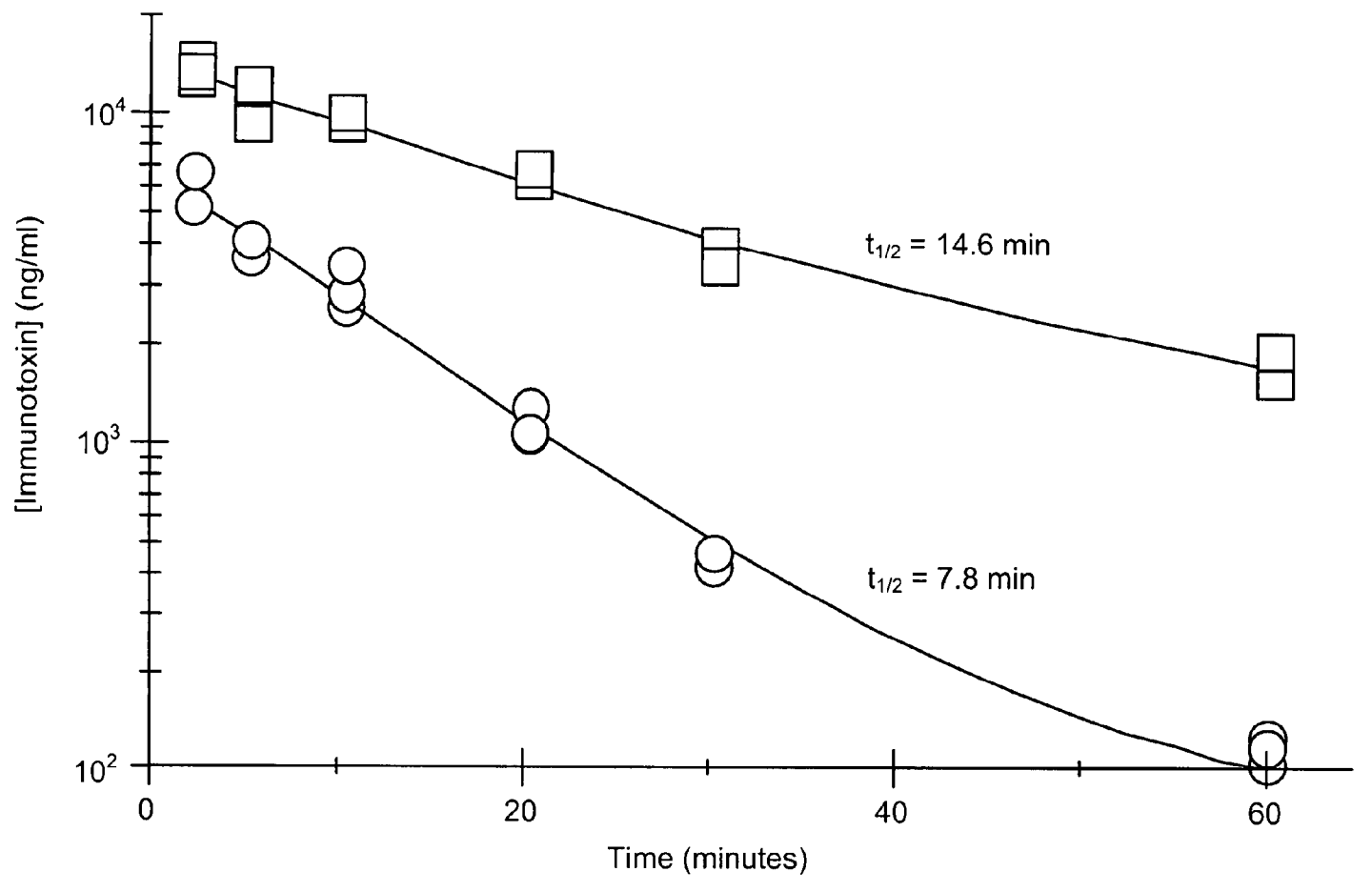

Balb/c mice were injected with 10 μg of either HA22 or HA22-LR and bled at intervals between 2 and 60 min. The concentration of immunotoxin in mouse serum was measured by ELISA. Data were fit to a single exponential decay function (FIG. 5). The half-life ($t_{1/2}$) of HA22 was 14.6 min (k=0.047), while the half-life of HA22-LR was 7.8 min (k=0.089).

TABLE 3

Nonspecific toxicity of HA22-LR

| Immunotoxin | Dose (mg/kg) | Dead/Total Mice |
|---|---|---|
| HA22 | 2.0 | 5/5 |
| HA22-LR | 2.5 | 0/12 |
|  | 5.0 | 0/4 |
|  | 10 | 0/10 |
|  | 20 | 0/10 |

Example 6

This Example sets forth the results of in vivo studies of HA22-LR on xenografts in mice.

Based on the comparability of the in vitro activity of HA22 and HA22-LR and the low animal toxicity of HA22-LR, the efficacy of HA22-LR was tested on a mouse xenograft tumor model. SCID mice with CA46 xenograft tumors averaging ~120 mm³ were treated intravenously QDD X 3 with PBS, 0.3 mg/kg HA22, or HA22-LR at doses of 1.0, 1.75, or 2.5 mg/kg.

Figure 6:
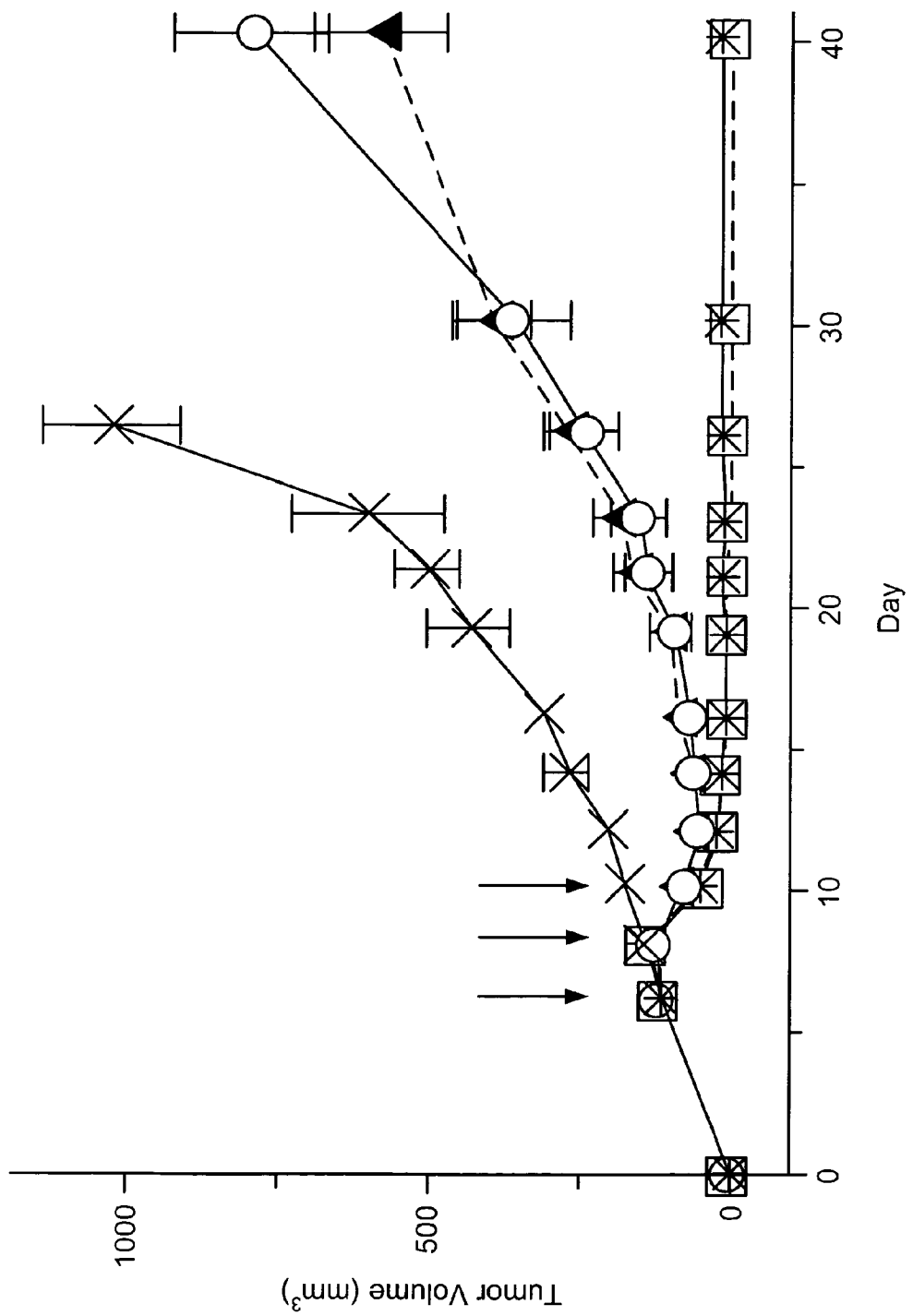

Tumor size was measured regularly for up to 40 days (FIG. 6) and observed visually for 10 weeks.

The tumors of PBS-treated mice rapidly grew to an average size greater than 1000 mm³ on day 26. Mice treated on days 6, 8 and 10 with 0.3 mg/kg HA22, the maximum dose that can be given to mice QOD X 3 without toxicity, caused regressions that brought the average tumor size to a minimum of ~52 mm³ on day 12. By day 21 all of the tumors had resumed rapid growth.

The tumor response to the 1.0 mg/kg dose of HA22-LR was similar to the response to 0.3 mg/kg HA22, but 1.75 mg/kg HA22-LR was much more effective. On day 14, 5/8 mice treated with 1.75 mg/kg HA22-LR had undetectable tumors that remained imperceptible for the duration of the study. The other tumors initially shrunk but grew to an average size of 54 mm³ on day 40. The 2.5 mg/kg dose of HA22-LR demonstrated a remarkable antitumor activity. In 7/8 mice the tumors completely disappeared by day 14 and had not returned by 10 weeks. One tumor diminished to 10 mm³ on day 14, but grew to 30 mm³ on day 40. We conclude that the low animal toxicity of HA22-LR allows larger doses of immunotoxin to be given safely, which dramatically enhances the antitumor activity of the immunotoxin.

Example 7

This Example discusses the results of studies using as the targeting moiety an antibody which binds an antigen called mesothelin present on the surface of many cancers.

An immunotoxin using the antibody, known as "SS1" (see, e.g., U.S. Pat. No. 7,081,518), as the targeting moiety, and PE38 as the toxin moiety, has been tested in a phase I clinical trial in patients with mesothelioma or ovarian cancer who had failed standard therapies (Hassan, R. et al., *Clin Cancer Res*, 13:5144-5149 (2007)). To compare the effect of using a lysosome-resistant PE of the invention, the PE used in the HA22-LR immunotoxin discussed in the preceding Examples was fused to antibody SS1 to form immunotoxin SS1-PE-LR and tested on mesothelin-expressing cell lines against a like immunotoxin of SS1 fused to PE38.

The results are shown in Table 4. As can be seen, for two of the cell lines, the cytotoxicity was comparable, while for one cell line, the immunotoxin with PE-LR was 3.72 times more cytotoxic to the cells than the immunotoxin made with PE38. On one cell line, the SS1-PE-LR immunotoxin had roughly half the cytotoxicity of the PE38 immunotoxin, indicating that it would be quite useful if it, like the HA22-LR immunotoxin, can be given at much higher doses without toxicity. The SS1-PE-LR immunotoxin had IC50 values in the single digit ng/ml range on 5 of the 6 cell lines tested. For one cell line, the SS1-PE-LR immunotoxin was much less cytotoxic to the cells than was the PE38-based immunotoxin. These results show that immunotoxins using PE-LR as the toxic moiety are likely to be useful therapeutic agents but, like most therapeutic agents, will not necessarily be useful against cells of all cancers or other disorders. The practitioner can readily determine whether any particular chimeric molecule using as the toxin moiety a PE of the invention will be effective on target cells, such as those of a patient's cancer, by taking a biopsy of the target cells to which the chimeric molecule is to be directed and testing the chimeric molecule on the biopsied cells to determine whether they are susceptible to having their growth inhibited by the chimeric molecule, with an IC50 in the single digit ng/mL range indicating that the growth inhibition is acceptable.

TABLE 4

Cytotoxicity of SS1-PE and SS1-PE-LR immunotoxin to cells of mesothelin-expressing cell lines.

| | | IC50 (ng/ml) | | |
| --- | --- | --- | --- | --- |
| Cell Line | Targeting moiety | Immunotoxin made with PE38 | Immunotoxin made with PE-LR | Relative Activity |
| L55 | SS1 | 4.77 ± 0.87 | 3.87 ± 0.41 | 1.23 |
| A1847 | SS1 | 4.06 ± 0.35 | 4.24 ± 0.28* | 0.96 |
| A431/K5 | SS1 | 0.20 ± 0.02 | 1.19 ± 0.19 | 0.17 |
| OVCAR-8 | SS1 | 2.32 ± 0.58 | 4.29 ± 0.67* | 0.54 |
| HAY | SS1 | 4.54 ± 0.59 | 1.22 ± 0.15 | 3.72 |
| KB31 | SS1 | 5.15 ± 0.57 | ≥1000* | ≥200× Decrease |

*Incomplete cell killing.

Example 8

This Example discusses the results of the studies set forth herein.

Deletion of protease-susceptible sites in PE produced a smaller form of PE that, in an exemplar immunotoxin, HA22-LR, maintained excellent cytotoxic activity on CD22-positive cell lines and on cells directly isolated from patients with HCL and CLL. In addition, HA22-LR was considerably less toxic to mice, demonstrating a greater than 10-fold reduction in non-specific toxicity. Previous studies in mice have shown that HA22 has a single-dose $LD_{50}$ of 1.33 mg/kg (Bang, S. et al., *Clin Cancer Res*, 11:1545-1550 (2005)). The studies underlying the present invention showed that a single intravenous dose of 2.0 mg/kg of HA22 killed 5/5 mice, but doses of HA22-LR up to 20 mg/kg did not kill any of the injected mice. This large decrease in animal toxicity allowed administration of much higher treatment doses, which led to greatly enhanced anti-tumor activity.

The nonspecific toxicity of immunotoxins in mice is primarily the result of liver damage (Kreitman, R. J. et al., *Blood*, 83:426-434 (1994); Onda, M. et al., *J Immunol*, 165:7150-7156 (2000); Onda, M. et al., *J Immunol*, 163:6072-6077 (1999); Onda, M. et al., *Cancer Res*, 61:5070-5077 (2001)), and toxicity in patients is also due in part to hepatic toxicity (Kreitman, R. J. et al., *J Clin Oncol*, 23:6719-6729 (2005); Hassan, R. et al., *Clin Cancer Res*, 13:5144-5149 (2007); Kreitman, R. J. et al., *N Engl J Med.*, 345:241-247 (2001); Kreitman, R. J. et al., *J Clin Oncol*, 18:1622-1636 (2000)). Mouse liver toxicity to LMB-2 (an immunotoxin targeted to the interleukin-2 receptor), and by extension all PE38 immunotoxins, is associated with the accumulation of the immunotoxin in Kupffer cells in the liver, which leads to the localized release of TNF-α and severe hepatotoxicity (Onda, M. et al., *J Immunol*, 165:7150-7156 (2000)). The low nonspecific toxicity of HA22-LR indicates that it lacks elements in HA22, presumably the segments removed from domains II and Ib, responsible for uptake by Kupffer cell and/or stimulation of TNF-α release. The removed segments, however, are not essential for anti-CD22 targeted toxicity, since HA22-LR retains anti-tumor activity similar to HA22.

Another factor that may contribute to the difference in nonspecific toxicity is the difference in the half lives of HA22 and HA22-LR (FIG. 5), which itself is likely due to more efficient filtration and removal of HA22-LR (51.0 kDa) than HA22 (63.3 kDa) by glomeruli in the kidney (Brenner, B. M. et al., *Am J Physiol*, 234:F455-F460 (1978)). The 2-fold difference in half life alone, however, is insufficient to explain the >10-fold difference in nonspecific toxicity. Previous efforts to reduce the nonspecific toxicity of immunotoxins have demonstrated that lowering the isoelectric point (pI) of the Fv in the immunotoxins LMB-2, B3(dsFv)-PE38, or SS1P decreases their nonspecific toxicity approximately 2- to 3-fold in mice (Onda, M. et al., *J Immunol*, 163:6072-6077 (1999); Onda, M. et al., *Cancer Res*, 61:5070-5077 (2001)). This observation does not account for the difference between HA22 and HA22-LR, since the two constructs have an identical Fv and the pI of HA22-LR is slightly increased relative to the pI of HA22 (pIHA22=5.26 and pIHA22-LR=5.63). In addition, the 2- to 3-fold difference in toxicity observed for this strategy is also much smaller than the >10-fold difference between HA22 and HA22-LR.

To produce the HA22-LR immunotoxin, lysosomal protease cleavage sites within PE38 were determined and deleted. Immunotoxin B3(dsFv)-PE38 was digested with both lysosomal extracts and Cathepsins B, D, and S, which have been implicated in antigen processing (Plüger, E. B. et al., *Eur J Immunol*, 32:467-476 (2002); Zhang, T. et al., *Immunology*, 100:13-20 (2000); Deussing, J. et al., *Proc Natl Acad Sci USA*, 95:4516-4521 (1998); Nakagawa, T. Y. et al., *Immunity*, 10:207-217 (1999); Shi, G. P. et al., *Immunity*, 10:197-206 (1999)). The lysosomal protease cleavage of PE-based immunotoxins was found to be concentrated within domains II and Ib of the PE38 toxin fragment. Prior work with native PE has shown that domain Ib is highly susceptible to limited proteolysis with chymotrypsin, Staphylococcal serine proteinase, pepsin A, and subtilisin (Bourdenet, S. et al., *Eur J Biochem*, 192:379-385 (1990)), confirming that domain Ib is easily accessible to proteases. The results herein show that domain II in PE38 is also protease accessible while domain III is less easily cleaved, probably due to a more compact, stable structure.

The information from the cleavage analysis was used to produce a series of deletions in the HA22 immunotoxin that, in the construct termed "M5" removed most of domains II and Ib, leaving only a short stretch of 11 amino acids from domain II (FIG. 3). This 11-residue fragment is composed of the amino acid sequence RHRQPRGWEQL (SEQ ID NO:11) and contains a furin protease cleavage site that is important for intracellular processing and activation of the native toxin (Ogata, M. et al., *J Biol Chem*, 265:20678-20685 (1990); Jinno, Y. et al., *J Biol Chem*, 264:15953-15959 (1989)). This construct, redesignated HA22-LR to emphasize its enhanced resistance to lysosomal proteases, is comprised of an anti-CD22 dsFv attached to a 25-kDa fragment of PE (PE25) containing the 11-residue fragment from domain II and all of domain III. When tested on several CD22-expressing cell lines, the activity of HA22-LR was similar to the HA22 immunotoxin from which it was derived.

Previous research has shown that domain Ib is not essential for the activity of PE immunotoxins (Siegall, C. B. et al., *J Biol Chem*, 264:14256-14261 (1989); Kihara, A. and Pastan, I., *Bioconjug Chem*, 5:532-538 (1994); Debinski, W. et al., *Mol Cell Biol*, 11:1751-1753 (1991); Kuan, C. T. and Pastan, I., *Proc Natl Acad Sci USA*, 93:974-978 (1996); Prior, T. I. et al., *Biochemistry*, 31:3555-3559 (1992)). Domain II, however, has been proposed to play a key role in membrane translocation during PE intoxication (Hwang, J. et al., *Cell*, 48:129-136 (1987); Prior, T. I. et al., *Biochemistry*, 31:3555-3559 (1992); Taupiac, M. P. et al., *Mol Microbiol*, 31:1385-1393 (1999); Wedekind, J. E. et al., *J Mol Biol*, 314:823-837 (2001); Méré, J. et al., *J Biol Chem*, 280:21194-21201 (2005)). The results reported herein indicates that a major component of the translocation activity of domain II may be localized to a short stretch of residues around the furin cleavage site. The data showing a 5-fold decrease in the activity of the M4 mutant, which eliminates the furin cleavage site, and previous work (Jinno, Y. et al., *J Biol Chem*, 264:15953-15959 (1989)) indicate that furin cleavage plays an important role in the cytotoxicity of PE. An additional possibility is that the resistance of HA22-LR to lysosomal degradation may compensate for any loss of translocation activity by allowing HA22-LR to survive longer within the cell. The cell surface targets of immunotoxins and the targeted cell type may also influence their intracellular trafficking and access to the cytosol.

HA22-LR had similar or slightly less cytotoxicity compared to HA22 on cells with high CD22 expression, including CD22-positive cells lines and fresh HCL cells. However, its cytotoxicity on CLL cells was more potent and more uniform than HA22. This may be due to the resistance of HA22-LR to lysosomal degradation leading to longer intracellular survival relative to HA22. It is unlikely that this was simply because HA22-LR survives longer than HA22 in the media during the 3-day incubation used in the studies, since other experiments have shown that HA22 has excellent stability in serum and in cell culture medium. It is possible that lysosomal protease digestion is a major mechanism of immunotoxin resistance for CLL cells, and that the HA22-LR molecule overcomes this resistance. Lysosomal protease digestion would also be present in cells with high CD22 expression, but may be treatment-limiting only in CLL, where CD22 expression is low and the relatively small number of internalized molecules limits immunotoxin activity. In addition, the activity of HA22-LR in CLL is very similar to that observed for HA22 in HCL, suggesting that HA22-LR should be developed further as potential treatment for this disease.

In addition to non-specific toxicities, another important factor limiting the usefulness of immunotoxins is the development of antibodies that react with the toxin and neutralize its activity. Other work from the laboratory of the present inventors recently described a mutant immunotoxin, HA22-8X, that is significantly less immunogenic in mice, because many, but not all, of the B cell epitopes have been removed. Fortunately, most of the remaining B cell epitopes in HA22-8X are located in the regions of domain II deleted in HA22-LR. Combining the mutations in both these molecules will produce an immunotoxin that is even less immunogenic.

HA22-LR has several advantages over HA22 that are expected to be applicable to other PE immunotoxins, but appears especially promising for the treatment of CLL. The nonspecific toxicity of HA22-LR in mice is more than 10-fold lower than HA22. The use of HA22-LR should therefore help to prevent treatment-related side effects and allow patients to receive higher doses for a better therapeutic outcome in humans. Additionally, the deletions used to generate HA22-LR eliminate known antibody epitopes and should help to limit the generation of neutralizing antibodies, allowing more treatment cycles to be given to patients. Relative to HA22, HA22-LR also has greatly enhanced, more uniform activity against patient-derived CLL cells, and generally similar activity on CD22-positive cell lines and HCL patient cells. For these reasons, HA22-LR represents an important advance in immunotoxin development.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated, mutated *Pseudomonas* exotoxin A (PE), comprising an amino acid sequence lacking all of domain II except for a furin cleavage sequence, and comprising an amino acid sequence of Formula I:

$R^1_n$-FCS-$R^2_n$-$R^3_n$-PE functional domain III    (Formula I)

wherein:
n=0 or 1, independently, for each of $R^1$, $R^2$ and $R^3$;
$R^1$=1 to 10 amino acid residues;
FCS=a furin cleavage sequence of 4 to 11 amino acid residues, which sequence is cleavable by furin and has an amino end and a carboxyl end, wherein the FCS:
(a) comprises an amino acid sequence of P4-P3-P2-P1 (Formula II), wherein P4 is an amino acid residue at the amino end, P3 is an amino acid residue, P2 is an amino acid residue, P1 is an amino acid residue at the carboxyl end, P1 is an arginine or a lysine residue, and the amino acid sequence is cleavable at the carboxyl end of P1 by furin; or
(b) is selected from SEQ ID NOs: 12-20; or
(c) is SEQ ID NO: 10, or a truncated version thereof comprising RQPR (SEQ ID NO: 21); or
(d) is SEQ ID NO: 11, or a truncated version thereof comprising RSKR (SEQ ID NO: 26);
$R^2$=1 to 10 amino acid residues;
$R^3$=1 or more contiguous amino acid residues of residues 365-394 of SEQ ID NO: 1; and
PE functional domain III=residues 395-613 of SEQ ID NO: 1, optionally comprising:
(i) a substitution of one or more of amino acid residues 609-613 as defined by reference to SEQ ID NO: 1;

(ii) a substitution of amino acid residue R490, as defined by reference to SEQ ID NO: 1, with glycine, alanine, valine, leucine, or isoleucine;
(iii) a substitution of one or more amino acid residues in an epitope or a subepitope of PE domain III; or
(iv) a combination of any of (i)-(iii).

2. The mutated PE of claim 1, Wherein the PCS comprises an amino acid sequence of Formula II:

P4-P3-P2-P1        (Formula II), wherein P4 is an amino acid residue at the amino end, P3 is an amino acid residue, P2 is an amino acid residue, P1 is an amino acid residue at the carboxyl end, P1 is an arginine residue or a lysine residue, and the amino acid sequence of Formula II is cleavable at the carboxyl end of P1 by furin.

3. The mutated PE of claim 2, wherein the FCS
  (i) further comprises amino acid residues represented by P6-P5 at the amino end;
  (ii) further comprises amino acid residues represented by P1'-P2' at the carboxyl end;
  (iii) P1 is an arginine residue or a lysine residue, P2' is tryptophan, and P4 is arginine, valine or lysine, provided that when P4 is not arginine, P6 and P2 are basic amino acid residues; and
  (iv) the sequence is cleavable at the carboxyl end of P1 by furin.

4. The mutated PE of claim 1, wherein the FCS is SEQ ID NO: 10.

5. The mutated PE of claim 1, wherein the PE functional domain III consists of amino acid residues 395 to 613 of SEQ ID NO: 1.

6. The mutated PE of claim 1, wherein n is 1 for $R^3$.

7. The mutated PE of claim 1, wherein n is 0 for $R^1$, $R^2$, and $R^3$.

8. The mutated PE of claim 1, wherein n is 0 for $R^3$.

9. The mutated PE of claim 8, wherein n is 1 for $R^1$ and $R^2$.

10. The mutated PE of claim 1, wherein n is 1 for $R^1$ and $R^2$.

11. An isolated, mutated *Pseudomonas* exotoxin A (PE), consisting of an amino acid sequence of Formula 1:

$R^1_n$-FCS-$R^2_n$-$R^3_n$-PE functional domain III        (Formula I)

wherein:
  n=0 or 1, independently, for each of $R^1$, $R^2$ and $R^3$;
  $R^1$=1 to 10 amino acid residues;
  FCS=a furin cleavage sequence of 4 to 11 amino acid residues, which sequence is cleavable by furin and has an amino end and a carboxyl end;
  $R^2$=1 to 10 amino acid residues;
  $R^3$=1 or more contiguous amino acid residues of residues 365-394 of SEQ ID NO: 1; and
  PE functional domain III=residues 395-613 of SEQ ID NO: 1, wherein the PE functional domain III is optionally modified to have
    (i) a substitution of one or more of amino acid residues 609-613 as defined by reference to SEQ ID NO: 1;
    (ii) a substitution of amino acid residue R490, as defined by reference to SEQ ID NO: 1, with glycine, alanine, valine, leucine, or isoleucine;
    (iii) a substitution of one or more amino acid residues in an epitope or a subepitope of PE domain III; or
    (iv) a combination of any of (i)-(iii).

12. The mutated PE of claim 11, wherein the FCS is an amino acid sequence of Formula II:

P4-P3-P2-P1        (Formula II), wherein P4 is an amino acid residue at the amino end, P1 is an amino acid residue at the carboxyl end, P1 is an arginine residue or a lysine residue, and the amino acid sequence of Formula II is cleavable at the carboxyl end of P1 by furin.

13. The mutated PE of claim 11, wherein the FCS is an amino acid sequence of Formula III:

P6-P5-P4-P3-P2-P1-P1'-P2'        (Formula III), wherein
  (i) P1 is an arginine residue or a lysine residue, P2' is tryptophan, and P4 is arginine, valine or lysine, provided that when P4 is not arginine, P6 and P2 are basic amino acid residues; and
  (ii) the sequence of Formula III is cleavable at the carboxyl end of P1 by furin.

14. The mutated PE of claim 11, wherein n is 0 for $R^3$.

15. The mutated PE of claim 11, wherein n is 1 for $R^1$ and $R^2$.

16. The mutated PE of claim 14, wherein n is 1 for $R^1$ and $R^2$.

17. The mutated PE of claim 11, wherein n is 0 for $R^1$, $R^2$, and $R^3$.

18. A chimeric molecule comprising
  (a) a ligand which specifically binds to an antigen or receptor on a cell surface, conjugated or fused to
  (b) the mutated PE of claim 11,
  wherein the ligand is not transforming growth factor α.

19. The chimeric molecule of claim 18, wherein the ligand is an antibody or fragment thereof which has antigen recognition capability.

20. A method of inhibiting growth of a target cell, the method comprising contacting the cell with the chimeric molecule of claim 18, wherein contacting the chimeric molecule to the cell inhibits the growth of the cell.

21. A chimeric molecule comprising
  (a) a ligand which specifically binds to an antigen or receptor on a cell surface, conjugated or fused to
  (b) a mutated *Pseudomonas* exotoxin A (PE) comprising an amino acid sequence lacking all of domain II except for a furin cleavage sequence, and comprising an amino acid sequence of Formula I:

$R^1_n$-FCS-$R^2_n$-$R^3_n$-PE functional domain III        (Formula I)

wherein:
  n=0 or 1, independently, for each of $R^1$, $R^2$ and $R^3$;
  $R^1$=1 to 10 amino acid residues;
  FCS=a furin cleavage sequence of 4 to 11 amino acid residues, which sequence is cleavable by furin and has an amino end and a carboxyl end, wherein the FCS:
    (a) comprises an amino acid sequence of P4-P3-P2-P1 (Forumla II), wherein P4 is an amino acid residue at the amino end, P3 is an ammino acid residue, P2 is an amino acid residue, P1 is an amino acid residue at the carboxyl end, P1 is an arginine or lysine resiude, and the amino acid sequence of Formula II is cleavable at the carboxyl end of P1 by furin; or
    (b) is selected from SEQ ID NOs: 12-20; or
    (c) is SEQ ID NO: 10, or a truncated version thereof comprising RQPR (SEQ ID NO: 21); or
    (d) is SEQ ID NO: 11, or a truncated version thereof comprising RSKR (SEQ ID NO: 26);
  $R^2$=1 to 10 amino acid residues;
  $R^3$=1 or more contiguous amino acid residues of residues 365-394 of SEQ ID NO: 1; and
  PE functional domain III=residues 395-613 of SEQ ID NO: 1, optionally comprising:
    (i) a substitution of one or more amino acid residues 609-613 as defined by reference to SEQ ID NO: 1;

(ii) a substitution of amino acid residue R490, as defined by reference to SEQ ID NO: 1, with glycine, alanine, valine, leucine, or isoleucine;

(iii) a substitution of one or more amino acid residues in an epitope or a subepitope of PE domain III; or (iv) a combination of any of (i)-(iii).

22. The chimeric molecule of claim 21, wherein the FCS comprises an amino acid sequence comprising of Formula II:

P4-P3-P2-P1 (Formula II), wherein P4 is an amino acid residue at the amino end, P3 is an amino acid residue, P2 is an amino acid residue, P1 is an amino acid residue at the carboxyl end, P1 is an arginine residue, and the amino acid sequence of Formula II is cleavable on the carboxyl end of P1 by furin.

23. The chimeric molecule of claim 22, wherein the FCS (i) further comprises amino acid residues represented by P6-P5 at the amino end, (ii) further comprises amino acid residues represented by P1'-P2' at the carboxyl end, (iii) P1 is an arginine residue, P2' is tryptophan, and P4 is arginine, valine or lysine, provided that when P4 is not arginine, then P6 and P2 are basic amino acid residues, and (iv) the sequence is cleavable at the carboxyl end of P1 by furin.

24. The chimeric molecule of claim 21, wherein the FCS is SEQ ID NO: 10.

25. The chimeric molecule of claim 21, wherein the PE functional domain III consists of amino acid residues 395 to 613 of SEQ ID NO: 1.

26. The chimeric molecule of claim 21, wherein n is 1 for $R^3$.

27. The chimeric molecule of claim 21, wherein n is 0 for $R^1$, $R^2$, and $R^3$.

28. The chimeric molecule of claim 21, wherein the ligand is an antibody or fragment thereof which has antigen recognition capability.

29. The chimeric molecule of claim 21, wherein n is 0 for $R^3$.

30. The chimeric molecule of claim 29, wherein n is 1 for $R^1$ and $R^2$.

31. The chimeric molecule of claim 21, wherein n is 1 for $R^1$ and $R^2$.

32. A method of inhibiting growth of a target cell having an exterior, the method comprising contacting the cell with a chimeric molecule, the chimeric molecule comprising:

(a) a ligand which specifically binds to an antigen or receptor on the exterior of the cell, wherein the ligand is conjugated or fused to (b) a mutated *Pseudomonas* exotoxin A (PE) comprising an amino acid sequence lacking all of domain II except for a furin cleavage sequence, and comprising an amino acid sequence of Formula I:

$R^1_n$-FCS-$R^2_n$-$R^3_n$-PE functional domain III (Formula I)

wherein:

n=0 or 1, independently, for each of $R^1$, $R^2$ and $R^3$;

$R^1$=1 to 10 amino acid residues;

FCS=a furin cleavage sequence of 4 to 11 amino acid residues, which sequence is cleavable by furin and has an amino end and a carboxyl end, wherein the FCS:

(a) comprises an amino acid sequence comprising P4-P3-P2-P1 (Formula II), wherein P4 is an amino acid residue at the amino end, P3 is an amino acid residue, P2 is an amino acid residue, P1 is an amino acid residue at the carboxyl end, P1 is an arginine or a lysine residue, and the amino acid sequence of Formula II is cleavable at the carboxyl end of P1 by furin; or (b) is selected from SEQ ID NOs: 12-20; or (c) is SEQ ID NO: 10, or a truncated version thereof comprising RQPR (SEQ ID NO: 21); or (d) is SEQ ID NO: 11, or a truncated version thereof comprising RSKR (SEQ ID NO: 26);

$R^2$=1 to 10 amino acid residues;

$R^3$=1 or more contiguous amino acid residues of residues 365-399 of SEQ ID NO: 1; and PE functional domain III=residues 395-613 of SEQ ID NO: 1, optionally comprising:

(i) a substitution of one or more of amino acid residues 609-613 as defined by reference to SEQ ID NO: 1;

(ii) a substitution of amino acid residue R490, as defined by reference to SEQ ID NO: 1, with glycine, alanine, valine, leucine, or isoleucine for arginine;

(iii) a substitution of one or more amino acid residues in an epitope or a subepitope of PE functional domain III; or (iv) a combination of any of (i)-(iii), and wherein the ligand is not transforming growth factor $\alpha$, and wherein contacting the chimeric molecule to the cell inhibits the growth of the cell.

33. The method of claim 32, wherein the FCS comprises an amino acid sequence of Formula II:

P4-P3-P2-P1 (Formula II), wherein P4 is an amino acid residue at the amino end, P3 is an amino acid residue, P2 is an amino acid residue, P1 is an amino acid residue at the carboxyl end, P1 is an arginine residue, and the amino acid sequence of Formula II is cleavable at the carboxyl end of P1 by furin.

34. The method of claim 33, wherein the FCS (i) further comprises amino acid residues represented by P6-P5 at the amino end;

(ii) further comprises amino acid residues represented by P1'-P2' at the carboxyl end, (iii) P1 is an arginine residue, P2' is tryptophan, and P4 is arginine, valine or lysine, provided that when P4 is not arginine, then P6 and P2 are basic amino acid residues; and (iv) the sequence is cleavable at the carboxyl end of P1 by farin.

35. The method of claim 32, wherein the FCS is SEQ ID NO: 10.

36. The method of claim 32, wherein the PE functional domain III consists of amino acid residues 395 to 613 of SEQ ID NO: 1.

37. The method of claim 32, wherein n is 1 for $R^3$.

38. The method of claim 32, wherein the ligand is an antibody or fragment thereof which has antigen recognition capability.

39. The method of claim 32, wherein n is 0 for $R^3$.

40. The method of claim 39, wherein n is 1 for $R^1$ and $R^2$.

41. The method of claim 32, wherein n is 1 for $R^1$ and $R^2$.

* * * * *